United States Patent [19]
Kato et al.

[11] Patent Number: 5,891,916
[45] Date of Patent: Apr. 6, 1999

[54] AROMATIC HYDROXAMIX ACID COMPOUNDS, THEIR PRODUCTION AND USE

[75] Inventors: Kaneyoshi Kato, Kawanishi; Yoshihiro Sugiura, Nara; Ken-ichi Naruo, Sanda; Hideki Takahashi, Osaka, all of Japan

[73] Assignee: Takeda Chemical Industries, Ltd., Osaka, Japan

[21] Appl. No.: 662,240

[22] Filed: Jun. 14, 1996

[30] Foreign Application Priority Data

Jun. 21, 1995 [JP] Japan ..... 7-154414

[51] Int. Cl.$^6$ ..... C07C 239/08; C07C 259/06; A61K 31/19; C07D 277/00
[52] U.S. Cl. ..... 514/575; 514/617; 514/620; 514/626; 514/618; 558/392; 558/312; 558/560; 560/45; 560/115; 560/320; 560/312; 564/300
[58] Field of Search ..... 558/392, 560, 558/312; 514/618, 626, 617, 620, 575; 560/45, 115; 564/300

[56] References Cited

U.S. PATENT DOCUMENTS

| | | | |
|---|---|---|---|
| 3,847,960 | 11/1974 | Avar et al. | 260/439 R |
| 4,681,894 | 7/1987 | Murray et al. | 514/507 |
| 5,180,742 | 1/1993 | Terao et al. | 514/558 |
| 5,272,180 | 12/1993 | Hashimoto et al. | 514/575 |
| 5,424,480 | 6/1995 | Vermehren et al. | 560/312 |

FOREIGN PATENT DOCUMENTS

| | | |
|---|---|---|
| 0256909 | 2/1988 | European Pat. Off. |
| 618221 | 3/1994 | European Pat. Off. |
| 0601477 | 6/1994 | European Pat. Off. |
| 2318118 | 10/1973 | Germany |
| 1050465 | 12/1966 | United Kingdom |
| 2276618 | 3/1994 | United Kingdom |

OTHER PUBLICATIONS

Lesslie Hellerman, J. Am. Chem. Soc. vol. 49, (1927), pp. 1735–1740.

Hale et al., J. Org. Chem., (1992), 57 (6), 1642–5.

CA 116:151391, (Database search, CAPLUS).

Qian et al., J. Am. Chem. Soc., (1996), vol. 39, No. 1, pp. 217–223.

Paaioannou et al., Acta Chemica Scandinavia 44 (1990) 189–194.

Bull. Soc. Chim. France, No. 204 (1956) 1345–1350.

Bull. Soc. Chim. France, No. 230 (1964) 1314–1317.

*Primary Examiner*—Jose' G. Dees
*Assistant Examiner*—Sabiha N. Qazi
*Attorney, Agent, or Firm*—Fitzpatrick, Cella, Harper & Scinto

[57] ABSTRACT

A compound represented by the formula:

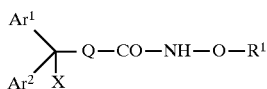

wherein $Ar^1$ and $Ar^2$ independently represent an optionally substituted aromatic group; Q represents an optionally substituted divalent aliphatic hydrocarbon group optionally containing O or S; $R^1$ represents H, acyl group, etc.; and X represents an electron-withdrawing group, an optionally substituted aromatic group, a group of the formula:

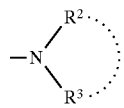

wherein $R^2$ and $R^3$ independently represent H, acyl group or an optionally substituted hydrocarbon group, etc., etc.; or salts thereof are useful as an excellent anti-neurodegenerative agent.

12 Claims, No Drawings

AROMATIC HYDROXAMIX ACID COMPOUNDS, THEIR PRODUCTION AND USE

TECHNICAL FIELD

This invention relates to novel aromatic hydroxamic acid derivatives and anti-neurodegenerative compositions. More specifically, the present invention relates to an aromatic hydroxamic acid derivative which is effective for the therapy and prophylaxis of encephalopathies, for example, neurodegenerative diseases such as Alzheimerrs disease, Down's syndrome and multiple sclerosis, etc., a process for producing the derivative and a pharmaceutical composition comprising the derivative, and so forth.

BACKGROUND ART

The cerebral nerve tissue represented by the cerebral cortex is made up of neurons governing sensory and perceptive functions and glia cells (astrocytes, oligodendrocytes and microglia) supporting the neurons, with the glia cells accounting for 90 percent of the whole tissue.

It was generally thought once that the central nervous system (CNS) is a static entity, and the immune system in this area is in a special environment (the so-called immune privilege). However, recent advances in molecular biological analysis have revealed that a variety of cytol,ines are produced and secreted intracerebrally and that the cellular or humoral immune system plays a pivotal role in the maintenance of homeostasis in the brain. At the same time, it has been suggested that excessive or abnormal activation of the immune system in CNS leads to the onset, progression and aggravation of various CNS diseases in the similar way as peripheral immune diseases.

Meanwhile, Alzheimer's disease (AD) is gathering increased attention these days as a type of dementia accompanied by degeneration and loss of neurons which is primarily found in persons of advanced age. With the increasing population of AD patients, the research and development work on drugs for the prevention and treatment of this disease is energetically pursued but the drugs so far developed are still providing only symptomatic relief at most and no fundamental drug therapy has been developed as yet.

In the intracerebral tissues of patients with Alzheimer's disease, accumulation of senile plaques and neurofibrillary tangles (NFT) are found and mentioned as a cause for the onset and progression of AD. Since deposits of β-amyloid protein (β-AP) are observed in senile plaques, it is clear that the β-AP deposition, followed by aggregation and formation of senile plaques is a chief etiologic factor in Alzheimer's diseases. Moreover, the finding of accumulation of microglial cells in activated state around senile plaques has led to the theory that the aggregation gains momentum as microglial cells attempt to phagocytize and eliminate β-AP and other deposits as foreign bodies and the formation of senile plaques is encouraged as a consequence. In senile plaques, complement deposits have also been found, and activation of the immune system has been pointed out as a cause for progression of AD morbidity and accompanying neuronal degeneration and loss. As it has thus been found that AD shares much with peripheral autoimmune diseases, it came to be regarded as an autoimmune disease of the brain. P. L. McGeer and co-workers, who paid attention to the epidemiologically low incidence of AD in patients with rheumatoid arthritis who received long-term anti-inflammatory drug therapy with an anti-inflammatory agent (indomethacin), and reported that the progression of AD could be supressed (WO 93/24115). Moreover, WO 93/08819 describes that lycoportine, an endogenous IL-1 antagonist, is useful for neurodegenerative diseases. However, since lycoportine is a macromolecular protein, the present inventors believe that it does not exhibit satisfactory stability or the absorption and transfer to the brain after oral administration.

Development of a novel compound having an excellent anti-neurodegenerative activity and being useful for the prophylaxis and therapy of encephalopathies has been ardently demanded.

U.S. Pat. No. 5,272,180, JP-A-1 104033 and JP-A-1 110624 describe quinone hydroxamic acid derivatives represented by the general formula:

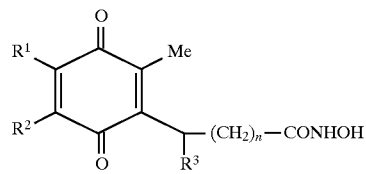

wherein $R^1$ and $R^2$ independently represent methyl group or methoxy group, or $R^1$ and $R^2$ are combined with each other to represent —CH=CH—CH=CH—; $R^3$ represents an optionally substituted aromatic group or heterocyclic group; and n denotes an integer of 2 to 8 (JP-A-1 110624), n denotes an integer of 5 or 6 (JP-A-1 104033), and their cell proliferation-inhibitory, neovascularization-inhibitory and autoimmune disease-ameliorating actions.

U.S. Pat. No. 5,180,742 and JP-A-61 44840 disclosed that a compound represented by the general formula:

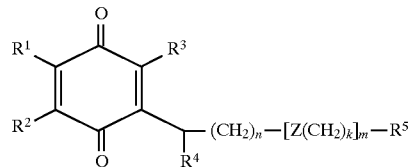

wherein $R^1$, $R^2$ and $R^3$ each represents e.g. hydrogen atom or methyl group; $R^4$ represents an optionally substituted aliphatic group, aromatic group or heterocyclic group; $R^5$ represents e.g. an optionally esterified or amidated carboxylic group; Z represents. e.g. —CH=CH—; n denotes an integer of 0 to 10; m denotes an integer of 0 to 3; and k denotes an integer of 0 to 5, has 5-lipoxygenase inhibitory activity and is of value as an antiasthmatic, antiallergic or cerebral circulation ameliorating agent.

Furthermore, Bulletin de la Societe Chimique France, pp.1345–1350 (1956) discloses production of compounds of the formula:

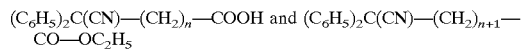

wherein n denotes an integer of 1 to 7 and, Bulletin de la Societe Chimique France, pp.1314–1317 (1964) discloses production of the compound of the formula:

However, these literature references do not discuss any medicinal effects of these compounds.

DISCLOSURE OF INVENTION

The inventors of the present invention, as a result of diligent research work, synthesized for the first time a compound having a group of specific chemical formula:

wherein each symbol is defined below, especially a group having two aromatic groups and an electron-withdrawing group substituted on the same carbon atom, which is represented by the formula:

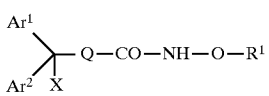 (I)

wherein $Ar^1$ and $Ar^2$ independently represent an optionally substituted aromatic group;

Q represents an optionally substituted divalent aliphatic hydrocarbon group optionally containing oxygen atom or sulfur atom;

$R^1$ represents hydrogen, an acyl group or an optionally substituted hydrocarbon group;

X represents i) an electron-withdrawing group, ii) an optionally substituted aromatic group, iii) a group of the formula:

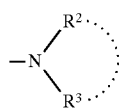

wherein $R^2$ and $R^3$ independently represent hydrogen, an acyl group or an optionally substituted hydrocarbon group, or $R^2$ and $R^3$, taken together with the adjacent nitrogen atom, may form an N-containing heterocyclic ring, iv) an optionally substituted hydroxy group or v) an optionally substituted mercapto group, or a salt thereof (hereinafter referred to as compound (I)), and discovered through a series of pharmaceutical and pharmacological experiments, that since these compounds have, based on this specific chemical structure, unexpectedly exhibit excellent anti-neurodegenerative activity and are of low toxicity, and will show therapeutic and prophylactic effects on encephalopathies.

More specifically, the present invention relates to:

(1) Compound (I);

(2) the compound of above (1) wherein Q is a divalent aliphatic hydrocarbon group optionally containing oxygen atom or sulfur atom, and X is an electron-withdrawing group, an optionally substituted aromatic group or a group of the formula:

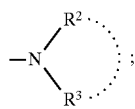

(3) the compound of above (1) wherein $Ar^1$ and $Ar^2$ are independently i) a $C_{6-14}$ aryl, ii) a 5- to 10-membered heteroaromatic group containing, besides carbon atoms, 1 to 4 hetero atoms selected from nitrogen, oxygen and sulfur or iii) a quinone group, each of which may be substituted by 1 to 5 substituents selected from the group consisting of halogen, $C_{1-3}$ alkylenedioxy, nitro, cyano, optionally halogenated $C_{1-6}$ alkyl, optionally halogenated $C_{3-6}$ cycloalkyl, optionally halogenated $C_{1-6}$ alkoxy, optionally halogenated $C_{1-6}$ alkylthio, hydroxyl, amino, mono-$C_{1-6}$ alkylamino, di-$C_{1-6}$ alkylamino, $C_{1-6}$ alkylcarbonyl, carboxyl, $C_{1-6}$ alkoxycarbonyl, carbamoyl, mono-$C_{1-6}$ alkylcarbamoyl, di-$C_{1-6}$ alkylcarbamoyl, $C_{6-10}$ arylcarbamoyl, sulfo, $C_{1-6}$ alkylsulfonyl, $C_{6-10}$ aryl, $C_{6-10}$ aryloxy, mono-$C_{1-6}$ alkylcarbamoyloxy and $C_{1-6}$ alkylcarboxamido, Q is (i) a divalent $C_{2-8}$ straight aliphatic hydrocarbon group or (ii) a group of the formula:

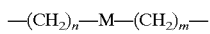

wherein M represents O, S, SO or $SO_2$, n and m independently represent an integer of 0 to 8 and n+m represents an integer of 2 to 8, each of which groups (i) and (ii) may be substituted by 1 to 5 $C_{1-6}$ alkyl groups, $R^1$ is i) hydrogen, ii) an acyl group represented by the formula: —CO—$R^4$, —CONH—$R^4$, —CO—O—$R^4$, —CS—NH—$R^4$ or —CS—O—$R^4$ wherein $R^4$ is a) hydrogen, b) a $C_{1-6}$ alkyl, $C_{2-6}$ alkenyl, $C_{2-6}$ alkynyl, $C_{3-6}$ cycloalkyl, $C_{6-14}$ aryl or $C_{7-16}$ aralkyl group, each of which may be substituted by 1 to 5 substituents selected from the group consisting of a halogen, $C_{1-3}$ alkylenedioxy, nitro, cyano, optionally halogenated $C_{1-6}$ alkyl, optionally halogenated $C_{3-6}$ cycloalkyl, optionally halogenated $C_{1-6}$ alkoxy, optionally halogenated $C_{1-6}$ alkylthio, hydroxyl, amino, mono-$C_{1-6}$ alkylamino, di-$C_{1-6}$ alkylamino, $C_{1-6}$ alkylcarbonyl, carboxyl, $C_{1-6}$ alkoxycarbonyl, carbamoyl, mono-$C_{1-6}$ alkylcarbamoyl, di-$C_{1-6}$ alkylcarbamoyl, sulfo, $C_{1-6}$ alkylsulfonyl, $C_{6-10}$ aryl, $C_{6-10}$ aryloxy and 5- or 6-membered heterocyclic group, or c) a 5- to 10-membered heterocyclic group containing, besides carbon atoms, 1 to 4 hetero atoms selected from nitrogen, oxygen and sulfur, which group may be substituted by 1 to 5 substituents selected from the group consisting of a halogen, $C_{1-3}$ alkylenedioxy, nitro, cyano, optionally halogenated $C_{1-6}$ alkyl, optionally halogenated $C_{3-6}$ cycloalkyl, optionally halogenated $C_{1-6}$ alkoxy, optionally halogenated $C_{1-6}$ alkylthio, hydroxyl, amino, mono-$C_{1-6}$ alkylamino, di-$C_{1-6}$ alkylamino, $C_{1-6}$ alkylcarbonyl, carboxyl, $C_{1-6}$ alkoxycarbonyl, carbamoyl, mono-$C_{1-6}$ alkylcarbamoyl, di-$C_{1-6}$ alkylcarbamoyl, sulfo, $C_{1-6}$ alkylsulfonyl, $C_{6-10}$ aryl, $C_{6-10}$ aryloxy and 5- or 6-membered heterocyclic group, or an acyl group represented by the formula: —$SO_2$—$R^{4a}$ or —SO—$R^{4a}$ wherein $R^{4a}$ is a) a $C_{1-6}$ alkyl, $C_{2-6}$ alkenyl, $C_{2-6}$ alkynyl, $C_{3-6}$ cycloalkyl, $C_{6-14}$ aryl or $C_{7-16}$ aralkyl group, each of which may be substituted by 1 to 5 substituents selected from the group consisting of a halogen, $C_{1-3}$ alkylenedioxy, nitro, cyano, optionally halogenated $C_{1-6}$ alkyl, optionally halogenated $C_{3-6}$ cycloalkyl, optionally halogenated $C_{1-6}$ alkoxy, optionally halogenated $C_{1-6}$ alkylthio, hydroxyl, amino, mono-$C_{1-6}$ alkylamino, di-$C_{1-6}$ alkylamino, $C_{1-6}$ alkylcarbonyl, carboxyl, $C_{1-6}$ alkoxycarbonyl, carbamoyl, mono-$C_{1-6}$ alkylcarbamoyl, di-$C_{1-6}$ alkylcarbamoyl, sulfo, $C_{1-6}$ alkylsulfonyl, $C_{6-10}$ aryl, $C_{6-10}$ aryloxy and 5- or 6-membered heterocyclic group, or b) a 5- to 10-membered heterocyclic group containing, besides carbon atoms, 1 to 4 hetero atoms selected from nitrogen, oxygen and sulfur, which group may be substituted by 1 to 5 substituents selected from the group consisting of a halogen, $C_{1-3}$ alkylenedioxy, nitro, cyano, optionally halogenated $C_{1-6}$ alkyl, optionally halogenated $C_{3-6}$ cycloalkyl, optionally halogenated $C_{1-6}$ alkoxy, optionally halogenated $C_{1-6}$ alkylthio, hydroxyl, amino, mono-$C_{1-6}$ alkylamino, di-$C_{1-6}$ alkylamino, $C_{1-6}$ alkylcarbonyl, carboxyl, $C_{1-6}$ alkoxycarbonyl, carbamoyl, mono-$C_{1-6}$ alkylcarbamoyl, di-$C_{1-6}$ alkylcarbamoyl, sulfo, $C_{1-6}$ alkylsulfonyl, $C_{6-10}$ aryl, $C_{6-10}$ aryloxy and 5- or 6-membered heterocyclic group, or iii) a $C_{1-6}$ alkyl, $C_{2-6}$ alkenyl, $C_{2-6}$ alkynyl, $C_{3-6}$ cycloalkyl, $C_{6-14}$ aryl or $C_{7-16}$ aralkyl group, each of which may be substituted by 1 to 5 substituents selected from the group consisting of a halogen, $C_{1-3}$ alkylenedioxy, nitro, cyano, optionally halogenated $C_{1-6}$ alkyl, optionally halogenated $C_{3-6}$ cycloalkyl, optionally halogenated $C_{16}$ alkoxy, optionally halogenated $C_{1-6}$ alkylthio, hydroxyl, amino, mono-$C_{1-6}$ alkylamino, $C_{1-6}$ alkylcarbonyl, carboxyl, $C_{1-6}$ alkoxycarbonyl, carbamoyl, mono-$C_{1-6}$ alkylcarbamoyl, di-$C_{1-6}$ alkylcarbamoyl, sulfo, $C_{1-6}$ alkylsulfonyl, $C_{6-10}$ aryl, $C_{6-10}$ aryloxy and 5- or 6-membered heterocyclic group, X is i) an electron-withdrawing group selected from the group consisting of a) a cyano group, b) an acyl group represented by the formula: —CO—$R^4$, —CONH—$R^4$, —CO—O—$R^4$, —CS—NH—$R^4$, —CS—O—$R^4$, —SO$_2$—$R^{4a}$ or —SO—$R^{4a}$ wherein $R^4$ and $R^{4a}$ are as defined above, c) a nitro group and d) a halogen, ii) a) a $C_{6-14}$ aryl, b) a 5- to 10-membered heteroaromatic group containing, besides carbon atoms, 1 to 4 hetero atoms selected from nitrogen, oxygen and sulfur or c) a quinone group, each of which group may be substituted by 1 to 5 substituents selected from the group consisting of a halogen, $C_{1-3}$ alkylenedioxy, nitro, cyano, optionally halogenated $C_{1-6}$ alkyl, optionally halogenated $C_{3-6}$ cycloalkyl, optionally halogenated $C_{1-6}$ alkoxy, optionally halogenated $C_{1-6}$ alkylthio, hydroxyl, amino, mono-$C_{1-6}$ alkylamino, di-$C_{1-6}$ alkylamino, $C_{1-6}$ alkylcarbonyl, carboxyl, $C_{1-6}$ alkoxycarbonyl, carbamoyl, mono-$C_{1-6}$ alkylcarbamoyl, di-$C_{1-6}$ alkylcarbamoyl, $C_{6-10}$ arylcarbamoyl, sulfo, $C_{1-6}$ alkylsulfonyl, $C_{6-10}$ aryl, $C_{6-10}$ aryloxy, mono-$C_{1-6}$ alkylcarbamoyloxy and $C_{1-6}$ alkylcarboxamido, iii) a group of the formula:

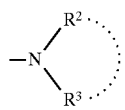

wherein $R^2$ and $R^3$ are independently a) hydrogen, b) an acyl group represented by the formula: —CO—$R^4$, —CONH—$R^4$, —CO—O—$R^4$, —CS—NH—$R^4$, —CS—O—$R^4$, —SO$_2$—$R^{4a}$ or —SO—$R^{4a}$ wherein $R^4$ and $R^{4a}$ are as defined above or c) a $C_{1-6}$ alkyl, $C_{2-6}$ alkenyl, $C_{2-6}$ alkynyl, $C_{3-6}$ cycloalkyl, $C_{6-14}$ aryl or $C_{7-16}$ aralkyl group, each of which may be substituted by 1 to 5 substituents selected from the group consisting of a halogen, $C_{1-3}$ alkylenedioxy, nitro, cyano, optionally halogenated $C_{1-6}$ alkyl, optionally halogenated $C_{3-6}$ cycloalkyl, optionally halogenated $C_{1-6}$ alkoxy, optionally halogenated $C_{1-6}$ alkylthio, hydroxyl, amino, mono-$C_{1-6}$ alkylamino, di-$C_{1-6}$ alkylamino, $C_{1-6}$ alkylcarbonyl, carboxyl, $C_{1-6}$ alkoxycarbonyl, carbamoyl, mono-$C_{1-6}$ alkylcarbamoyl, di-$C_{1-6}$ alkylcarbamoyl, sulfo, $C_{1-6}$ alkylsulfonyl, $C_{6-10}$ aryl, $C_{6-10}$ aryloxy and 5- or 6-membered heterocyclic group, or $R^2$ and $R^3$, taken together with the adjacent nitrogen atom, form a 5- to 7-membered N-containing ring, besides carbon atoms, having one nitrogen atom and optionally having 1 to 3 hetero atoms selected from nitrogen, oxygen and sulfur, which group may be substituted by 1 to 5 substituents selected from the group consisting of a halogen, $C_{1-3}$ alkylenedioxy, nitro, cyano, optionally halogenated $C_{1-6}$ alkyl, optionally halogenated $C_{3-6}$ cycloalkyl, optionally halogenated $C_{1-6}$ alkoxy, optionally halogenated $C_{1-6}$ alkylthio, hydroxyl, amino, mono-$C_{1-6}$ alkylamino, di-$C_{1-6}$ alkylamino, $C_{1-6}$ alkylcarbonyl, carboxyl, $C_{1-6}$ alkoxycarbonyl, carbamoyl, mono-$C_{1-6}$ alkylcarbamoyl, di-$C_{1-6}$ alkylcarbamoyl, sulfo, $C_{1-6}$ alkylsulfonyl, $C_{6-10}$ aryl, $C_{6-10}$ aryloxy and 5- or 6-membered heterocyclic group, c) a 5- to 10-membered heterocyclic group containing, besides carbon atoms, 1 to 4 hetero atoms selected from nitrogen, oxygen and sulfur, which group may be substituted by 1 to 5 substituents selected from the group consisting of a halogen, $C_{1-3}$ alkylenedioxy, nitro, cyano, optionally halogenated $C_{1-6}$ alkyl, optionally halogenated $C_{3-6}$ cycloalkyl, optionally halogenated $C_{1-6}$ alkoxy, optionally halogenated $C_{1-6}$ alkylthio, hydroxyl, amino, mono-$C_{1-6}$ alkylamino, di-$C_{1-6}$ alkylamino, $C_{1-6}$ alkylcarbonyl, carboxyl, $C_{1-6}$ alkoxycarbonyl, carbamoyl, mono-$C_{1-6}$ alkylcarbamoyl, di-$C_{1-6}$ alkylcarbamoyl, sulfo, $C_{1-6}$ alkylsulfonyl, $C_{6-10}$ aryl or $C_{6-10}$ aryloxy and 5- or 6-membered heterocyclic group, or d) an acyl group represented by the formula: —CO—$R^4$, —CONH—$R^4$, —CO—O—$R^4$, —CS—NH—$R^4$, —CS—O—$R^4$, —SO$_2$—$R^{4a}$ or —SO—$R^{4a}$, or v) a group of the formula: —SR$^6$ wherein R$^6$ is a) hydrogen,. b) a $C_{1-6}$ alkyl, $C_{2-6}$ alkenyl, $C_{2-6}$ alkynyl, $C_{3-6}$ cycloalkyl, $C_{6-14}$ aryl or $C_{7-16}$ aralkyl group, each of which may be substituted by 1 to 5 substituents selected from the group consisting of a halogen, $C_{1-3}$ alkylenedioxy, nitro, cyano, optionally halogenated $C_{1-6}$ alkyl, optionally halogenated $C_{3-6}$ cycloalkyl, optionally halogenated $C_{1-6}$ alkoxy, optionally halogenated $C_{1-6}$ alkylthio, hydroxyl, amino, mono-$C_{1-6}$ alkylamino, di-$C_{1-6}$ alkylamino, $C_{1-6}$alkylcarbonyl, carboxyl, $C_{1-6}$ alkoxycarbonyl, carbamoyl, mono-$C_{1-6}$ alkylcarbamoyl, di-$C_{1-6}$ alkylcarbamoyl, sulfo, $C_{1-6}$ alkylsulfonyl, $C_{6-10}$ aryl, $C_{6-10}$ aryloxy and 5- or 6-membered heterocyclic group, c) a 5- to 10-membered heterocyclic group containing, besides carbon atoms, 1 to 4 hetero atoms selected from nitrogen, oxygen and sulfur, which group may be substituted by 1 to 5 substituents selected from the group consisting of a halogen, $C_{1-3}$ alkylenedioxy, nitro, cyano, optionally halogenated $C_{1-6}$ alkyl, optionally halogenated $C_{3-6}$ cycloalkyl, optionally halogenated $C_{1-6}$ alkoxy, optionally halogenated $C_{1-6}$ alkylthio, hydroxyl, amino, mono-$C_{1-6}$ alkylamino, di-$C_{1-6}$ alkylamino, $C_{1-6}$ alkylcarbonyl, carboxyl, $C_{1-6}$ alkoxycarbonyl, carbamoyl, mono-$C_{1-6}$ alkylcarbamoyl, di-$C_{1-6}$ alkylcarbamoyl, sulfo, $C_{1-6}$ alkylsulfonyl, $C_{6-10}$ aryl, $C_{6-10}$ aryloxy and 5- or 6-membered heterocyclic group, or d) an acyl group represented by the formula: —CO—$R^4$, —CONH—$R^4$, —CO—O—$R^4$, —CS—NH—$R^4$, —CS—O—$R^4$, —$SO_2$—$R^{4a}$ or —SO—R wherein $R^4$ and $R^{4a}$ are as defined above;

(4) the compound of above (3) wherein the aromatic groups for $Ar^1$ and $Ar^2$ are independently phenyl, naphthyl, pyridyl, quinolyl, isoquinolyl, benzothiazolyl, thienyl or thiazolyl;

(5) the compound of above (3) wherein Q is $C_{2-8}$ alkylene group;

(6) the compound of above (3) wherein $R^1$ is hydrogen or an acyl group represented by the formula: —CO—$R^4$, —CONH—$R^4$, —CO—O—$R^4$, —CS—NH—$R^4$ or —CS—O—$R^4$ wherein $R^4$ is as defined in above;

(7) the compound of above (3) wherein X is an electron-withdrawing group;

(8) the compound of above (3) wherein X is a cyano group or an acyl group represented by the formula: —CO—$R^4$, —CONH—$R^4$, —CO—O—$R^4$, —CS—NH—$R^4$, —CS—O—$R^4$, —$SO_2$—$R^{4a}$ or —SO—$R^{4a}$ wherein $R^4$ and $R^{4a}$ are as defined above;

(9) the compound of above (3) wherein $Ar^1$ and Ar2 are independently a phenyl, 1-naphthyl, 2-naphthyl, 2-pyridyl, 3-pyridyl, 4-pyridyl, 2-quinolyl, 3-quinolyl, 4-quinolyl, 5-quinolyl, 8-quinolyl, 2-benzothiazolyl, 2-thienyl, 2-thiazolyl or 1-isoquinolyl group, each of which may be substituted by 1 to 3 substituents selected from the group consisting of a halogen and an optionally halogenated $C_{1-6}$ alkoxy,
Q is $C_{4-6}$ alkylene group,
$R^1$ is hydrogen or an acyl group represented by the formula: —CO—$R^{4'}$ or —CONH—$R^{4'}$ wherein $R^{4'}$ is a $C_{1-6}$ alkyl, $C_{6-14}$ aryl or mono-cyclic N-containing aromatic group which may be substituted by 1 to 3 substituents selected from the group consisting of a halogen, an optionally halogenated $C_{1-6}$ alkyl and an optionally halogenated $C_{1-6}$ alkoxy, and
X is a cyano group;

(10) the compound of above (1) wherein $Ar^1$ and $Ar^2$ are independently a phenyl, 2-naphthyl, 2-pyridyl, 2-benzothiazolyl, 2-quinolyl, 2-thienyl or 2-thiazolyl group, each of which may be substituted by 1 to 3 substituents selected from the group consisting of a halogen, optionally halogenated $C_{1-3}$ alkyl, optionally halogenated $C_{1-3}$ alkoxy, hydroxyl and mono-$C_{1-6}$ alkylcarbamoyloxy,
Q is a straight $C_{4-6}$ alkylene group or —$(CH_2)_3SCH_2$—, $R^1$ is hydrogen or an acyl group represented by the formula: —CO—$R^{4'''}$ or —CONH—$R^{4'''}$ wherein $R^{4'''}$ is i) hydrogen or ii) a $C_{1-6}$ alkyl, phenyl or pyridyl group, each of which may be substituted by a $C_{1-6}$ alkoxy group, and
X is i) a cyano group, ii) an acyl group represented by the formula: —CO—O—$R^{4''''}$ wherein $R^{4''''}$ is a $C_{1-6}$ alkyl group or iii) a phenyl group;

(11) the compound of above (1) which is
7-cyano-7,7-diphenylheptanohydroxamic acid,
7,7-bis(4-methoxyphenyl)-7-cyanoheptanohyroxamic acid,
7,7-bis(4-fluorophenyl)-7-cyanoheptanohydroxamic acid,
O-propionyl-7-cyano-7,7-diphenylheptanohydroxamic acid,
O-propionyl-7,7-bis(4-methoxyphenyl)-7-cyanoheptanohydroxamic acid,
O-propionyl-7,7-bis(4-fluorophenyl)-7-cyanoheptanohydroxamic acid,
O-benzoyl-7-cyano-7,7-diphenylheptanohydroxamic acid,
O-benzoyl-7,7-bis(4-methoxyphenyl)-7-cyanoheptanohydroxamic acid,
O-benzoyl-7,7-bis(4-fluorophenyl)-7-cyanoheptanohydroxamic acid,
7-cyano-7,7-bis(4-ethoxyphenyl)heptanohydroxamic acid,
7-cyano-7,7-bis[4-(2,2,2-trifluoroethoxyphenyl)] heptanohydroxamic acid, 7-cyano-7-phenyl-7-(2-pyridyl) heptanohydroxamic acid, or a salt thereof;

(12) a process for producing a compound (I), which comprises reacting a compound of the formula:

(II)

wherein all symbols are as defined above or a salt thereof or a reactive derivative thereof at the carboxyl group with hydroxylamine, and if necessary, allowing the resultant compound to react with a compound of the formula:

wherein Y represents a leaving group and $R^{1a}$ represents an acyl group or an optionally substituted hydrocarbon group or a salt thereof;

(13) a pharmaceutical composition which comprises the compound (I), if necessary together with a pharmaceutically acceptable carrier;

(14) the composition of above (13) which is an anti-neurodegenerative composition;

(15) the composition of above (13) which is for preventing or treating neurodegenerative diseases;

(16) the composition of above (15) which is for preventing or treating Alzheimer's disease or multiple sclerosis, and so forth.

In the above formulae, the "aromatic group" of the "optionally substituted aromatic group" shown by $Ar^1$ or $Ar^2$ includes, for example, aromatic hydrocarbon groups, aromatic heterocyclic groups, and quinone groups. Preferably, aromatic hydrocarbon groups and aromatic heterocyclic groups are mentioned.

The "aromatic hydrocarbon groups" mentioned above include, for example, $C_{6-14}$ monocyclic or condensed polycyclic aromatic hydrocarbon groups. Specific examples of them include $C_{6-14}$ aryl groups such as phenyl, 1-naphthyl, 2-naphthyl, indenyl and anthryl. Among others, phenyl, 1-naphthyl and 2-naphthyl are preferred.

Examples of the "aromatic heterocyclic groups" include 5- to 10-membered monocyclic or the corresponding fused aromatic heterocyclic groups containing, besides carbon atom, one or more (e.g. 1 to 4) hetero-atoms selected from nitrogen atom, sulfur atom and oxygen atom. Specific examples of the aromatic heterocyclic groups mean monovalent groups formed by eliminating an optional hydrogen atom from the aromatic heterocyclic ring which can be fused with one or more (preferably one or two) aromatic rings (e.g. benzene ring). Specific example of the rings include thiophene, benzo[b]thiophene, benzo[b]furan, benzimidazole, benzoxazole, benzothiazole, benzisothiazole, naphtho[2,3-b]thiophene, thianthrene, furan, isoindolizine, xanthene, phenoxathiin, pyrrole, imidazole, pyrazole, pyridine, pyrazine, pyrimidine, pyridazine, indole, isoindole, 1H-indazole, purine, 4H-quinolizine, isoquinoline,. quinoline, phthalazine, naphthyridine, quinoxaline, quinazoline, cinnoline, carbazole, β-carboline, phenanthridine, acridine, phenazine, thiazole, isothiazole, phenothiazine, isoxazole, furazan, phenoxazine and isochroman. Preferred examples of the "aromatic heterocyclic group" include 2-pyridyl, 3-pyridyl, 4-pyridyl, 2-quinolyl, 3-quinolyl, 4-quinolyl, 5-quinolyl, 8-quinolyl, 1-isoquinolyl, 3-isoquinolyl, 4-isoquinolyl, 5-isoquinolyl, 1-indolyl, 2-indolyl, 3-indolyl, 2-benzothiazolyl, 2-benzo[b]thienyl, benzo[b]furanyl, 2-thienyl, 3-thienyl and 2-thiazolyl. More preferable examples include 2-pyridyl, 3-pyridyl, 4-pyridyl, 2-quinolyl, 3-quinolyl, 4-quinolyl, 5-quinolyl, 8-quinolyl, 2-benzothiazolyl, 1-isoquinolyl, 2-thienyl and 2-thiazolyl.

The "quinone group" means a group available on elimination of one hydrogen atom from a quinone ring, which is exemplified by p-benzoquinone, 1,4-naphthoquinone, anthraquinone, 5,6-chrysenequinone and 5,8-dioxo-5,8-dihydroquinoline.

Examples of the substituent for "optionally substituted aromatic groups" include, for example, halogen atoms (e.g. fluorine, chlorine, bromine and iodine), $C_{1-3}$ alkylenedioxy groups (e.g. methylenedioxy and ethylenedioxy), nitro group, cyano group, optionally halogenated $C_{1-6}$ alkyl groups, optionally halogenated $C_{3-6}$ cycloalkyl groups, optionally halogenated $C_{1-6}$ alkoxy groups, optionally halogenated $C_{1-6}$ alkylthio group, hydroxyl group, amino group, mono-$C_{1-6}$ alkylamino groups (e.g. methylamino, ethylamino, propylamino, isopropylamino and butylamino), di-$C_{1-6}$ alkylamino groups (e.g. dimethylamino, diethylamino, dipropylamino and dibutylamino), $C_{1-6}$ alkylcarbonyl groups (e.g. acetyl and propionyl), carboxyl group, $C_{1-6}$ alkoxycarbonyl groups (e.g. methoxycarbonyl, ethoxycarbonyl, propoxycarbonyl and butoxycarbonyl), carbamoyl group, mono-$C_{1-6}$ alkylcarbamoyl groups (e.g. methylcarbamoyl and ethylcarbamoyl), di-$C_{1-6}$ alkylcarbamoyl groups (e.g. dimethylcarbamoyl and diethylcarbamoyl), $C_{6-10}$ arylcarbamoyl (e.g. phenylcarbamoyl and naphthylcarbamoyl), sulfo group, $C_{1-6}$ alkylsulfonyl groups (e.g. methylsulfonyl and ethylsulfonyl), $C_{6-10}$ aryl groups (e.g. phenyl and naphthyl), $C_{6-10}$ aryloxy groups (e.g. phenyloxy and naphthyloxy), mono-$C_{1-6}$ alkylcarbamoyloxy groups (e.g. methylcarbamoyloxy and ethylcarbamoyloxy) and mono-$C_{1-6}$ alkylcarboxamido groups (e.g. methylcarboxamido and ethylcarboxamido).

The above-mentioned "optionally halogenated $C_{1-6}$ alkyl groups" include, for example, $C_{1-6}$ alkyl groups. (e.g. methyl, ethyl, propyl, isopropyl, butyl, isobutyl, sec-butyl, tert-butyl, pentyl and hexyl) optionally having 1 to 3 halogen atoms (e.g. fluorine, chlorine, bromine and iodine). Thus, for example, methyl, chloromethyl, difluoromethyl, trichloromethyl, trifluoromethyl, ethyl, 2-bromoethyl, 2,2,2-trifluoroethyl, pentafluoroethyl, propyl, 3,3,3-trifluoropropyl, isopropyl, butyl, 4,4,4-trifluorobutyl, isobutyl, sec-butyl, tert-butyl, pentyl, isopentyl, neopentyl, 5,5,5-trifluoropentyl, hexyl and 6,6,6-trifluorohexyl can be mentioned.

The above-mentioned "optionally halogenated $C_{3-6}$ cycloalkyl groups" include, for example, $C_{3-6}$ cycloalkyl groups (e.g. cyclopropyl, cyclobutyl, cyclopentyl and cyclohexyl) optionally having 1 to 3 halogen atoms (e.g. fluorine, chlorine, bromine and iodine). Thus, for example, cyclopropyl, cyclobutyl, cyclopentyl, cyclohexyl, 2,2,3,3-tetrafluorocyclopentyl and 4-chlorocyclohexyl can be mentioned.

The above-mentioned "optionally halogenated $C_{1-6}$ alkoxy groups" include, for example, $C_{1-6}$ alkoxy groups (e.g. methoxy, ethoxy, propoxy, butoxy, isobutoxy, sec-butoxy, tert-butoxy and pentyloxy) optionally having 1 to 3 halogen atoms (e.g. fluorine, chlorine, bromine and iodine). Thus, for example, methoxy, difluoromethoxy, trifluoromethoxy, ethoxy, 2,2,2-trifluoroethoxy, propoxy, isopropoxy, butoxy, 4,4,4-trifluorobutoxy, isobutoxy, sec-butoxy, pentyloxy and hexyloxy can be mentioned.

The above-mentioned "optionally halogenated $C_{1-6}$ alkylthio groups" include, for example, $C_{1-6}$ alkylthio groups" (e.g. methylthio, ethylthio, propylthio, isopropylthio, n-butylthio, sec-butylthio and tert-butylthio) optionally having 1 to 3 halogen atoms (e.g. fluorine, chlorine, bromine and iodine). Thus, for example, methylthio, difluoromethylthio, trifluoromethylthio, ethylthio, propylthio, isopropylthio, butylthio, 4,4,4-trifluorobutylthio, pentylthio and hexylthio can be mentioned.

The "aromatic group" for the "optionally substituted aromatic groups" may have 1 to 5, preferably 1 to 3, substituents at possible positions of the ring and, when the number of substituents is two or more, those substituents may be the same as or different from one another.

The preferred substituent for the "optionally substituted aromatic groups" shown by $Ar^1$ or $Ar^2$ include, for example, 1 to 3 halogen atoms, optionally halogenated $C_{1-6}$ alkyl groups, optionally halogenated $C_{1-6}$ alkoxy groups, cyano group, hydroxyl group and mono-$C_{1-6}$ alkylcarbamoyloxy groups.

The "divalent aliphatic hydrocarbon group optionally containing oxygen atom or sulfur atom" for the "optionally substituted divalent aliphatic hydrocarbon group optionally containing oxygen atom or sulfur atom" shown by Q is formed by, for example, eliminating one each of hydrogen atom bonding to different two carbon atoms of a saturated or unsaturated aliphatic hydrocarbon, which is a divalent group optionally containing one or two, preferable one, oxygen atom or sulfur atom at a position between carbon atoms or the terminal position. Among others, preferred is the straight groups having 2 to 8 carbon atoms.

Specific examples include;

(i) $C_{2-8}$ alkylene groups (e.g. —$CH_2$, —$(CH_2)_2$—, —$(CH_2)_3$—, —$(CH_2)_4$—, —$(CH_2)_5$—, —$(CH_2)_6$—, —$(CH_2)_7$—, —$(CH_2)_8$—, etc.)

(ii) $C_{2-8}$ alkenylene groups (e.g. —$CH_2$—CH=CH—, —$CH_2$—CH=CH—$CH_2$—, —$CH_2$—$CH_2$—CH=CH—, —CH=CH—$CH_2$—$CH_2$—$CH_2$— and —$CH_2$—$CH_2$—$CH_2$—$CH_2$—CH=CH—, etc.)

(iii) alkynylene groups (e.g. —C≡C—, —$CH_2$—C≡C—, —$CH_2$—C≡C—$CH_2$—$CH_2$-, etc.)

(iv) a group of the formula: —$(CH_2)_n$—M—$(CH_2)_m$— wherein M represents O, S, SO or $SO_2$, n and m independently represent an integer of 0 to 8 (preferably 1 to 4), and n+m represents an integer of 2 to 8.

More preferable examples include $C_{3-7}$ alkylene groups (e.g. trimethylene, tetramethylene, pentamethylene and hexamethylene), $C_{2-6}$ alkenylene groups (e.g. vinylene, propenylene, butenylene and hexanylene) and $C_{3-7}$ alkynylene (e.g. propynylene, butanylene and pentanylene). Among these groups, straight $C_{4-6}$ ones are especially preferable. Among others, straight $C_{4-6}$ alkylene groups optionally having one sulfur atom are also preferred.

The substituent for "optionally substituted divalent aliphatic hydrocarbon group optionally containing oxygen atom or sulfur atom" includes, for example $C_{1-6}$ alkyl groups such as methyl, ethyl, propyl, isopropyl, butyl, isobutyl, sec-butyl, tert-butyl, pentyl and hexyl. The "optionally substituted divalent aliphatic hydrocarbon group optionally containing oxygen atom or sulfur atom" may have 1 to 5 substituents mentioned above at possible positions of the group and, when the number of substituents is two or more, those substituents may be the same as or different from one another.

The "acyl group" shown by $R^1$, $R^2$ or $R^3$ include, for example, an acyl group represented by the formula: —CO—$R^4$, —CONH—$R^4$, —CO—O—$R^4$, —CS—NH—$R^4$ or —CS—O—$R^4$ wherein $R^4$ represents hydrogen, an optionally substituted hydrocarbon group or an optionally substituted heterocyclic group, or an acyl group represented by the formula: —$SO_2$—$R^{4a}$ or —SO—$R^{4a}$ wherein $R^{4a}$ represents an optionally substituted hydrocarbon group or an optionally substituted heterocyclic group. Among these groups, —CO—$R^4$, —CONH—$R^4$, —CO—$OR^4$ and —CS—O—$R^4$ wherein $R^4$ is of the same meaning as defined above are preferable.

The "hydrocarbon groups" for the "optionally substituted hydrocarbon groups" shown by $R^1$, $R^2$, $R^3$, $R^4$ or $R^{4a}$ mean a group which is available upon elimination of one hydrogen atom from a hydrocarbon compounds, as exemplified by chain-like or cyclic hydrocarbon groups such as alkyl groups, alkenyl groups, cycloalkyl groups, aryl groups and aralkyl groups. Among them, the following $C_{1-6}$ chain-like or cyclic hydrocarbon groups are preferable.

a) $C_{1-6}$ alkyl groups (e.g. methyl, ethyl, propyl, isopropyl, butyl, isobutyl, sec-butyl, tert-butyl, pentyl and hexyl), b) $C_{2-6}$ alkenyl groups (e.g. vinyl, allyl, isopropenyl; butenyl, isobutenyl and sec-butenyl), c) $C_{2-6}$ alkynyl groups (e.g. propargyl, ethynyl, butynyl and 1-hexynyl), d) $C_{3-6}$ cycloalkyl groups (e.g. cyclopropyl, cyclobutyl, cyclopentyl and cyclohexyl optionally condensed with benzene ring optionally having one to three $C_{1-6}$ alkoxy groups (e.g. methoxy)), e) $C_{6-14}$ aryl groups (e.g. phenyl, 1-naphthyl, 2-naphthyl, biphenyl, 2-indenyl and 2-anthryl), preferably phenyl group, f) $C_{7-16}$ aralkyl groups (e.g. benzyl, phenethyl, diphenylmethyl, triphenylmethyl, 1-naphthylmethyl, 2-naphthylmethyl, 2-diphenylethyl, 3-phenylpropyl, 4-phenylbutyl and 5-phenylpentyl), preferably benzyl group.

Among these groups, $C_{1-6}$ alkyl groups and $C_{6-14}$ aryl groups are preferable.

Examples of the "substituent" for the "optionally substituted hydrocarbon group" include, for example, halogen atoms (e.g. fluorine, chlorine, bromine and iodine), $C_{1-3}$ alkylenedioxy groups (e.g. methylenedioxy and ethylenedioxy), nitro group, cyano group, optionally halogenated $C_{1-6}$ alkyl groups, optionally halogenated $C_{3-6}$ cycloalkyl groups, optionally halogenated $C_{1-6}$ alkoxy groups, optionally halogenated $C_{1-6}$ alkylthio groups, hydroxyl group, amino group, mono-$C_{1-6}$ alkylamino groups (e.g. methylamino and ethylamino), di-$C_{1-6}$ alkylamino groups (e.g. dimethylamino and diethylamino), $C_{1-6}$ alkylcarbonyl groups (e.g. acetyl and ethylcarbonyl), carboxyl group, $C_{1-6}$ alkoxycarbonyl groups (e.g. methoxycarbonyl, ethoxycarbonyl, propoxycarbonyl and butoxycarbonyl), carbamoyl group, mono-$C_{1-6}$ alkylcarbamoyl groups (e.g. methylcarbamoyl and ethylcarbamoyl), di-$C_{16}$ alkylcarbamoyl groups (e.g. dimethylcarbamoyl and diethylcarbamoyl), sulfo group, $C_{1-6}$ alkylsulfonyl groups (e.g. methylsulfonyl and ethylsulfonyl), $C_{6-10}$ aryl groups (e.g. phenyl), $C_{6-10}$ aryloxy groups (e.g. phenyloxy) and 5- or 6-membered heterocyclic groups.

The "optionally halogenated $C_{1-6}$ alkyl groups", "optionally halogenated $C_{3-6}$ cycloalkyl groups", "optionally halogenated $C_{1-6}$ alkoxy groups" and "optionally halogenated $C_{1-6}$ alkylthio groups" mentioned above include, for example, those described in detail in the foregoing referring to the substituents of the aromatic groups shown by $Ar^1$ or $Ar^2$.

The "5- or 6-membered heterocyclic groups" mentioned above include, for example, 5- or 6-membered heterocyclic groups each containing, besides the carbon atom, 1 to 3 hetero-atoms selected from nitrogen atom, oxygen atom and sulfur atom. Specific examples include, for example, 1, 2- or 3-pyrrolidinyl, 2- or 4-imidazolinyl, 2-, 3- or 4-pyrazolidinyl, piperidino, 2-, 3- or 4-piperidyl, 1- or 2-piperazinyl, morpholino, 2-thienyl, 3-thienyl, 2-pyridyl, 4-pyridyl, 2-furyl, 3-furyl, pyrazinyl, 2-pyrimidinyl, 3-pyrrolyl, 3-pyridazinyl, 3-isothiazolyl and 3-isoxazolyl.

The "hydrocarbon group" for the "optionally substituted hydrocarbon group" may have 1 to 5, preferably 1 to 3 of, for example, the above-mentioned substituents at any possible position, and, when two or more substituents are present, they may the same as or different from one another.

The "heterocyclic group" for the "optionally substituted heterocyclic group" shown by $R^4$ includes, for example, 5- to 10-membered (monocyclic or condensed dicyclic) heterocyclic groups each containing, besides carbon atom, preferably 1 to 4 hetero-atoms of 1 or 2 species selected from nitrogen atom, oxygen atom and sulfur atom. Examples of the group include, for example, non-aromatic heterocyclic groups such as 1-, 2- or 3-pyrrolidinyl, 2- or 4-imidazolinyl, 2-, 3- or 4-pyrazolidinyl, piperidino, 2-, 3- or 4-piperidyl, 1-or 2-piperazinyl and morpholinyl; or aromatic heterocyclic groups such as 2- or 3-thienyl, 2-, 3- or 4-pyridyl, 2- or 3-furyl, 2-, 3-, 4-, 5- or 8-quinolyl, 1-, 3- or 4-isoquinolyl, pyrazinyl, 2- or 4-pyrimidinyl, 3-pyrrolyl, 2-imidazolyl, 3-pyridazinyl, 3-isothiazolyl, 3-isoxazolyl, 1-indolyl and 2-isoindolyl. Among these groups, aromatic heterocyclic groups are preferred. Still more preferable examples include 5- or 6-membered aromatic heterocyclic groups each containing, besides carbon atom, 1 to 3 hetero-atoms selected from nitrogen atom oxygen atom and sulfur atom (e.g. 2-thienyl, 3-thienyl, 2-pyridyl, 3-pyridyl and 4-pyridyl). Especially preferred are mono-cyclic (5- or 6-membered) N-containing aromatic groups such as 2-pyridyl, 3-pyridyl, 4-pyridyl, 2-pyrrolyl, 2-imidazolyl, 2-pyrazinyl, 2-pyrimidinyl and 4-pyrimidinyl. Most preferred is 2-pyridyl.

The substituent which may be optionally present on the "heterocyclic group" for the "optionally substituted heterocyclic group" may be similar, in kind and number, to the substituent optionally present on the "optionally substituted hydrocarbon group" shown by $R^4$.

The "electron-withdrawing group" shown by X includes, for example, cyano group, acyl groups, nitro group and halogen atoms.

The above-mentioned "acyl groups" include, for example, those acyl groups mentioned for $R^1$, $R^2$ or $R^3$.

The "optionally substituted aromatic group" shown by X includes, for example, those optionally substituted aromatic group mentioned for $Ar^1$ or $Ar^2$.

The "N-containing heterocyclic ring" for the "optionally substituted N-containing heterocyclic ring" formed by, taken together with the adjacent nitrogen atom, $R^2$ and $R^3$ include, for example, 5- to 7-membered nitrogen-containing rings each, besides carbon atom, having one nitrogen atom and optionally having 1 to 3 hetero-atoms selected from nitrogen atom, oxygen atom and sulfur atom. Specific examples include piperidine, morpholine, thiomorpholine, piperazine, N-methylpiperazine, 2-oxoazetidine, 2-oxopyrrolidine and 2-oxopiperidine.

The "substituent" for the "optionally substituted N-containing heterocyclic ring", may be similar, in kind and number, to the substituent optionally present on the "optionally substituted aromatic group" shown by $Ar^1$ or $Ar^2$.

The "optionally substituted hydroxy group" shown by X includes, for example, a group represented by the formula: —$OR^5$ wherein $R^5$ represents hydrogen, an optionally substituted hydrocarbon group, an optionally substituted heterocyclic group or an acyl group.

The "optionally substituted hydrocarbon group" and "optionally substituted heterocyclic group" shown by $R^5$ respectively include, for example, those optionally substituted hydrocarbon group and optionally substituted heterocyclic group mentioned for $R^4$, respectively.

The "acyl groups" shown by $R^5$ includes, for example, ones similar to the above-mentioned "acyl groups" shown by $R^1$.

The "optionally substituted mercapto group" shown by X includes, for example, a group represented by the formula: —$SR^6$ wherein $R^6$ is ones similar to the above $R^5$.

In the compound (I), $Ar^1$ or $Ar^2$ is preferably (i) an optionally substituted $C_{6-14}$ aryl group or (ii) an optionally substituted 5- to 10-membered monocyclic or condensed aromatic heterocyclic group containing, besides carbon atom, one or more hetero-atoms selected from nitrogen atom, sulfur atom and oxygen atom. More preferable examples include a phenyl, 1-naphthyl, 2-naphthyl, 2-pyridyl, 3-pyridyl, 4-pyridyl, 2-quinolyl, 3-quinolyl, 4-quinolyl, 5-quinolyl, 8-quinolyl, 2-benzothiazolyl, 1-isoquinolyl, 2-thienyl or 2-thiazolyl group, each of which may be substituted by 1 to 4 substituents selected from a group consisting of halogen atom, $C_{1-3}$ alkylenedioxy groups, nitro group, cyano group, optionally halogenated $C_{1-6}$ alkyl groups, optionally halogenated $C_{3-6}$ cycloalkyl groups, optionally halogenated $C_{1-6}$ alkoxy groups, optionally halogenated $C_{1-6}$ alkylthio groups, hydroxyl group, amino group, mono-$C_{1-6}$ alkylamino groups, di-$C_{1-6}$ alkylamino groups, $C_{1-6}$ alkylcarbonyl groups, carboxyl group, $C_{1-6}$ alkoxycarbonyl groups, carbamoyl group, mono-$C_{1-6}$ alkylcarbamoyl groups, di-$C_{1-6}$ alkylcarbamoyl groups, sulfo group, $C_{1-6}$ alkylsulfonyl groups, $C_{6-10}$ aryl group and $C_{6-10}$ aryloxy group.

Q is preferably a $C_{2-8}$ alkylene group.

$R^1$ is preferably hydrogen atom or an acyl group. More preferred is an acyl group. Preferable examples of the acyl group include the group represented by —CO—$R^4$, —CONH—$R^4$, —CO—O—$R_4$, —CS—NH—$R^4$ or —CS—O—$R^4$ wherein $R^4$ is hydrogen, an optionally substituted hydrocarbon group or an optionally substituted heterocyclic group. Among others, —CO—$R^4$ and —CONH—$R^4$ wherein $R^4$ is of the same meaning as defined above are especially preferable.

Preferable examples of $R^4$ include (i) an optionally substituted $C_{1-6}$ alkyl group, (ii) an optionally substituted $C_{6-14}$ aryl group or (iii) an optionally substituted mono-cyclic N-containing aromatic group.

X is preferably an electron-withdrawing group. More preferred is cyano group or an acyl group. Preferable acyl group is represented by —CO—O—$R^4$. Especially preferable example of X is cyano group.

Preferred are compounds such that, in the formula (I), $Ar^1$ and $Ar^2$ are independently a phenyl, 1-naphthyl, 2-naphthyl, 2-pyridyl, 3-pyridyl, 4-pyridyl, 2-quinolyl, 3-quinolyl, 4-quinolyl, 5-quinolyl, 8-quinolyl, 2-benzothiazolyl, 2-thienyl, 2-thiazolyl or 1-isoquinolyl group, each of which may be substituted by 1 to 3 substituents selected from the group consisting of halogen atom, $C_{1-3}$ alkylenedioxy group, nitro group, cyano group, an optionally halogenated $C_{1-6}$ alkyl group, an optionally halogenated $C_{3-6}$ cycloalkyl group, an optionally halogenated $C_{1-6}$ alkoxy group, an optionally halogenated $C_{1-6}$ alkylthio group, hydroxyl group, amino group, mono-$C_{1-6}$ alkylamino group, di-$C_{1-6}$ alkylamino group, $C_{1-6}$ alkylcarbonyl group, carboxyl group, $C_{1-6}$ alkoxycarbonyl group, carbamoyl group, mono-$C_{1-6}$ alkylcarbamoyl group, di-$C_{1-6}$ alkylcarbamoyl group, sulfo group, $C_{1-6}$ alkylsulfonyl group, $C_{6-10}$ aryl group and $C_{6-10}$ aryloxy group, Q is a $C_{2-8}$ alkylene group, $R^1$ is hydrogen or an acyl group, and X is an electron-withdrawing group.

Still more preferred are compounds in which $Ar^1$ and $Ar^2$ are independently a phenyl, 1-naphthyl, 2-naphthyl, 2-pyridyl, 3-pyridyl, 4-pyridyl, 2-quinolyl, 3-quinolyl, 4-quinoly, 5-quinolyl, 8-quinolyl, 2-benzothiazolyl, 2-thienyl, 2-thiazolyl or 1-isoquinolyl group, each of which may be substituted by halogen atom or an optionally halogenated $C_{1-6}$ alkoxy group, Q is a straight $C_{4-6}$ alkylene group, $R^1$ is hydrogen atom or an acyl group represented by the formula: —CO—$R^4$ or —CONH—$R^4$, $R^4$ is (i) a $C_{1-6}$ alkyl group, (ii) a $C_{6-14}$ aryl group or (iii) a mono-cyclic N-containing aromatic group, each of which may be substituted by halogen, optionally halogenated $C_{1-6}$ alkyl groups or optionally halogenated $C_{1-6}$ alkoxy groups, and X is cyano group.

The following is a partial list of the preferred species of compound (I).

7-cyano-7,7-diphenylheptanohydroxamic acid,
7,7-bis(4-methoxyphenyl)-7-cyanoheptanohydroxamic acid,
7,7-bis(4-fluorophenyl)-7-cyanoheptanohydroxamic acid,
O-propionyl-7-cyano-7,7-diphenylheptanohydroxamic acid,
O-propionyl-7,7-bis(4-methoxyphenyl)-7-cyanoheptanohydroxamic acid,
O-propionyl-7,7-bis(4-fluorophenyl)-7-cyanoheptanohydroxamic acid,
O-benzoyl-7-cyano-7,7-diphenylheptanohydroxamic acid,
O-benzoyl-7,7-bis(4-methoxyphenyl)-7-cyanoheptanohydroxamic acid,
O-benzoyl-7,7-bis(4-fluorophenyl)-7-cyanoheptanohydroxamic acid,
7-cyano-7,7-bis(4-ethoxyphenyl)heptanohydroxamic acid,
7-cyano-7,7-bis[4-(2,2,2-trifluoroethoxyphenyl)]heptanohydroxamic acid,
7-cyano-7-phenyl-7-(2-pyridyl)heptanohydroxamic acid,
or a salt thereof.

As the salts of compound (I) of this invention, for example, salts with inorganic bases, salts with organic bases, salts with inorganic acids, salts with organic acids and salts with basic or acidic amino acids can be mentioned. Preferable examples of salts with inorganic bases include alkali metal salts such as sodium salt and potassium salt; alkaline earth metal salts such as calcium salts, magnesium salts and barium salts; transitional metal salts such as zinc salts, iron salts and copper salts; and aluminum salts and ammonium salts. Preferred salts with organic bases are exemplified by salts with trimethylamine, triethylamine, pyridine, picoline, ethanolamine, diethanolamine, triethanolamine, dicyclohexylamine or N,N'-dibenzylethylenediamine. Preferred salts with inorganic acids are exemplified by salts with hydrochloric acid, hydrobromic acid, nitric acid, sulfuric acid or phosphoric acid. Preferred salts with organic acids are exemplified by salts with formic acid, acetic acid, trifluoroacetic acid, fumaric acid, oxalic acid, tartaric acid, maleic acid, citric acid, succinic acid, malic acid, methanesulfonic acid, benzenesulfonic acid or p-toluenesulfonic acid. Preferred salts with basic amino acids are exemplified by salts with arginine, lysine or ornithine. Preferred salts with acidic amino acids are exemplified by salts with aspartic acid or glutamic acid.

Among others, pharmaceutically acceptable salts are preferable. Preferable examples include, for example, inorganic salts such as alkali metal salts (e.g. sodium salt and potassium salt), alkaline earth metal salts (e.g. calcium salt, magnesium salt and barium salt), and transitional metal salts such as zinc salts, iron salts and copper salts, and ammonium salts; and when the compound (I) has a basic functional group, inorganic salts such as hydrochloride, sulfate, phosphate and hydrobromide, or, organic salts such as acetate, maleate, fumarate, succinate, methane-sulfonate, p-toluenesulfonate, citrate and tartrate.

Process for producing the compound (I) or a salts thereof of this invention (hereinafter simply referred to as "compound (I)" are described below.

The compound (I) can be synthesized, as a starting material using the corresponding carboxylic acid compound (II), by a procedure analogous to those described in JP-A-1 104033 and S. Patai (ed.): Supplement B. The chemistry of acid derivatives, Vol. 2 (John Wiley & Sons), pp.849–873 (1992).

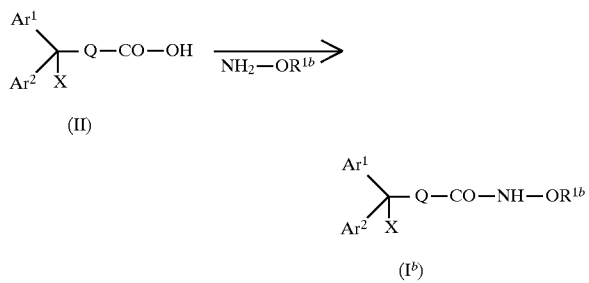

For example, the compound (II) is converted to a reactive derivative of its carboxyl group, which is then allowed to react with hydroxylamine in the presence of a base at temperatures ranging from 0° to 50° C., preferably at room temperatures (0° to 30° C.), for about 10 minutes to 2 hours to provide the compound ($I^b$).

The reactive derivative includes, for example, acid anhydride, acid halide and activated ester.

The hydroxylamine can be, for example, a compound represented by the formula: $NH_2$—$OR^{1b}$ wherein $R^{1b}$ represents hydrogen atom or an optionally substituted hydrocarbon group or a salt thereof (e.g. hydrochloride).

The "optionally substituted hydrocarbon group" shown by $R^{1b}$ can be ones similar to those defined in reference to $R^1$.

The base mentioned above includes inorganic bases such as alkali metal or alkaline earth metal salts of hydrogencarbonic acid e.g. sodium hydrogencarbonate and potassium hydrogencarbonate, alkali metal or alkaline earth metal salts of carbonic acid e.g. sodium carbonate and potassium carbonate and alkali metal or alkaline earth metal hydroxides e.g. sodium hydroxide, potassium hydroxide and calcium hydroxide; and organic bases such as alkylamines e.g. triethylamine and diisopropylethylamine.

The amount of the hydroxylamine is at least one equivalent, preferably 2 to 5 equivalents, relative to the compound (II). The amount of the base is at least two times as much equivalents, preferably about 4 to 10 equivalents, relative to the hydroxylamine then employed.

The solvent for this reaction is one which does not interfere with the reaction, as exemplified by water, alcohols (e.g. methanol, ethanol, n-propanol and isopropanol), nitriles (e.g. acetonitrile), halogenated hydrocarbons (e.g. dichloromethane and chloroform), ethers (e.g. diethyl ether, tetrahydrofuran and dioxane). These solvents can be used each alone or in a suitable mixture.

The reaction temperature ranges from about 0° to 50° C., preferably room temperature. The reaction time ranges from about 10 minutes to 2 hours. The compound ($I^b$) can also be produced by allowing a lower alkyl ester of the compound (II) to react with hydroxylamine in the presence of a base. This reaction can be carried out by a per se known procedure, for example, the procedure described in Shin Jikken Kagaku Koza compiled by The Chemical Society of Japan, Vol.14, p.1227.

As the hydroxylamines mentioned above is, for example, the compounds represented by the above-mentioned compound of the formula $NH_2$—$OR^{1b}$ or salts thereof.

The base mentioned above includes strong bases such as alkali metal or alkaline earth metal hydrides (e.g. lithium hydride, sodium hydride, potassium hydride and calcium hydride), alkali metal or alkaline earth metal amides (e.g. lithium amide, sodium amide, lithium diisopropyl amide, lithium dicyclohexyl amide, lithium hexamethyl silazide, sodium hexamethyl silazide and potassium hexamethyl silazide) and alkali metal or alkaline earth metal lower alkoxides (e.g. sodium methoxide, sodium ethoxide and potassium t-butoxide); inorganic bases such as alkali metal or alkaline earth metal hydroxides (e.g. sodium hydroxide, potassium hydroxide, lithium hydroxide and barium hydroxide), alkali metal or alkaline earth metal carbonates (e.g. sodium carbonate, potassium carbonate and cesium carbonate) and alkali metal or alkaline earth hydrogencarbonates (e.g. sodium hydrogencarbonate and potassium hydrogencarbonate); and organic bases such as amines e.g. triethylamine, diisopropyl ethylamine, N-methyl morpholine, dimethyl aminopyridine, DBU (1,8-diazabicyclo[5.4.0]-7-undecene) and DBN (1.5-diazabicyclo[4.3.0]non-5-ene) or basic heterocyclic compounds e.g. pyridine, imidazole and 2,6-lutidine. Among others, strong bases such as alkali metal or alkaline earth metal lower alkoxides (e.g. sodium methoxide, sodium ethoxide and potassium t-butoxide) are preferable.

The amount of the hydroxylamines relative to the lower alkyl ester is at least equimolar, preferably ranges from about 3 to 20 equivalents.

The amount of the base may be an excess relative to hydroxylamine, for example, about 1.2 to 2 equivalents.

The solvent for this reaction can be any one which does not interfere with the reaction, as exemplified by alcohols (e.g. methanol, ethanol, n-propanol, isopropanol, tert-butanol, ethylene glycol and sec-butanol) and ethers (e.g. diethyl ether, tetrahydrofuran and dioxane). These solvents can be used each alone or as a suitable mixture of two or more species.

The reaction temperature ranges from about −20° C. to 50° C., and is preferably room temperature. The reaction time ranges from about 1 to 18 hours.

When $R^{1b}$ is hydrogen, the compound ($I^a$) is produced by subjecting the compound ($I^{b'}$) to acylation or alkylation.

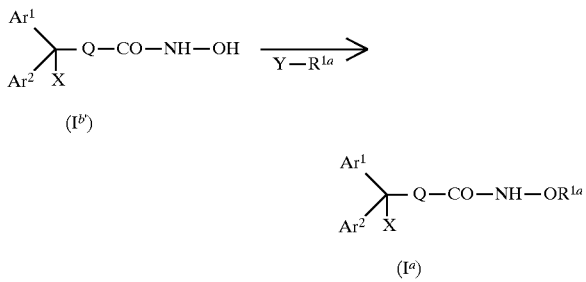

For example, the compound ($I^{b'}$) is allowed to react with a compound represented by the formula Y—$R^{1a}$ wherein Y represents a leaving group, and $R^{1a}$ represents an acyl group or an optionally substituted hydrocarbon group or a salt thereof to give the compound ($I^a$). The "leaving group" shown by Y includes, for example, halogen atoms (e.g. chlorine, bromine and iodine), a $C_{1-4}$ alkylsulfonyloxy group optionally substituted by 1 to 3 halogen atoms (e.g. methanesulfonyloxy and trifluoromethanesulfonyloxy), a $C_{6-10}$. arylsulfonyloxy group optionally substituted by 1 to 4 halogen atoms (e.g. p-toluenesulfonyloxy, benzenesulfonyloxy, p-bromobenzenesulfonyloxy and mesitylenesulfonyloxy), a $C_{1-6}$ alkoxy group (e.g. methoxy, ethoxy, propoxy, isopropoxy and butoxy), a $C_{6-10}$ aryloxy group optionally having 1 to 3 substituents selected from halogen atoms and nitro group (e.g. phenoxy, p-chlorophenoxy and p-nitrophenoxy).

The "acyl group" and the "optionally substituted hydrocarbon group" shown by $R^{1a}$ include those defined in reference to $R^1$.

The acylation reaction can be carried out by a per se known procedure, for example, the procedure described in Journal of Organic Chemistry, Vol. 26, p.782 (1961). For example, the compound ($I^{b'}$) or a salt thereof or a reactive derivative thereof is allowed to react with a compound represented by the formula: Y—$R^{1a'}$ wherein $R^{1a'}$ represents an acyl group or a salt thereof in the presence of a base.

The reactive derivative includes, for example, acid anhydride, acid halide, activated ester and lower alkyl ester.

The base includes, for example, alkylamines such as triethylamine and diisopropylethylamine, and nitrogen-containing aromatic heterocyclic compounds such as pyridine.

The amount of the above compound of the formula: Y—$R^{1a'}$ or a salt thereof ranges from about 1 to 1.2 equivalents relative to the compound ($I^{b'}$).

The amount of the base ranges from about 1 to 3 equivalents relative to the above compound of the formula: Y—$R^{1a'}$.

The solvent for this reaction can be any one which does not interfere with the reaction, as exemplified by nitrites (e.g. acetonitrile), halogenated hydrocarbons (e.g. dichloromethane and chloroform), ethers (e.g. diethyl ether, tetrahydrofuran, dioxane, isopropyl ether and 1,2-dimethoxyethane).

The reaction temperature ranges from about −20° C. to room temperature, and is preferably room temperature. The reaction time can be appropriately selected depending on the reagents then employed, which ranges, for example, from about 0.2 to 5 hours.

The reaction may also be conducted by dissolving both the compound ($I^{b'}$) and an approximately equimolar amount of the corresponding organic acid (i.e. a compound of the formula $R^{1a}$—OH) in an inert solvent (e.g. halogenated hydrocarbons or acetonitriles) and by allowing the reaction to proceed in the presence of about 1 to 1.5 equivalent of a dehydrative condensing agent such as dicyclohexyl carbodiimide. The reaction time ranges from about −20° C. to room temperature and the reaction time ranges from about 6 to 12 hours.

The carbamoylation reaction can be carried out under substantially the same conditions as the above-described acylation reaction not necessarily in the co-presence of a base.

The compound ($I^a$) can be produced by subjecting the compound ($I^{b'}$) to alkylation, for example, alkylation described in "Comprehensive Organic Transformation" authored by Richard C. Larock published by VCH Publishers Inc. or an analogous procedure thereto.

The compound (II) can be produced by a method described in the above-mentioned Bulletin de la Societe Chimique France, pp.1345–1350 (1956) or ibid. pp.1314–1317 (1964) or analogous methods thereto.

As one of the practical examples, mention is made of the following method, with no intention of limiting thereto.

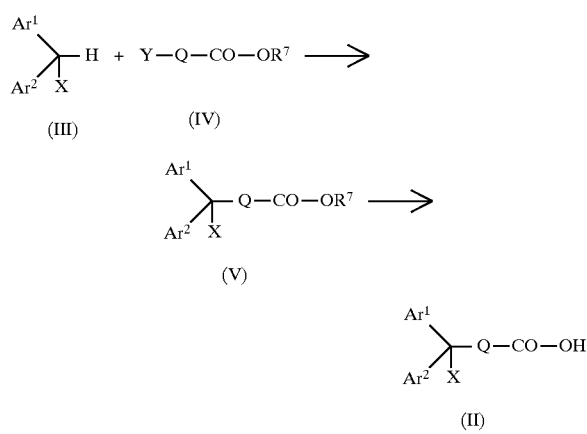

wherein $R^7$ represents a lower alkyl group and other symbols are of the same meaning as defined above.

The compound (II) can be obtained by, for example, subjecting the compound (III) to substitution reaction with the compound (IV) to give the compound (V), and then by subjecting the compound (V) to hydrolysis.

The above substitution reaction can be conducted in the presence of a base.

The base mentioned above includes, for example, the above-mentioned strong bases, inorganic bases and organic bases. Among others, strong bases are preferable. As inorganic bases, potassium carbonate and sodium carbonate are preferable. As organic bases, DBU is preferable.

The amount of the base ranges from about 1 to 5, preferably about 1 to 3, equivalents relative to the compound (III).

The amount of the compound (IV) ranges from about 1 to 3 equivalents relative to the compound (III).

The solvent for this reaction can be any solvent which does not interfere with the reaction, as exemplified by alcohols (e.g. methanol and ethanol), ethers (e.g. diethyl ether, tetrahydrofuran (THF) and dioxane), halogenated hydrocarbons (e.g. dichloromethane, 1,2-dichloroethane, chloroform and carbon tetrachloride), aromatic hydrocarbons (e.g. benzene, toluene and xylene), nitrites (e.g. acetonitrile), acid amides (e.g. N,N-dimethylformamide), ketones (e.g. acetone and methyl ethyl ketone), and sulfoxides (e.g. dimethyl sulfoxide). These solvents can be used each alone or as a mixture of two or more species. Among others, ethers (e.g. THF and diethyl ether), nitrites (e.g. acetonitrile), acid amides (e.g. N,N-dimethylformamide) and ketones (e.g. acetone) are preferred.

The reaction temperature ranges from about 0° C. to 100° C., preferably from about 10° C. to 50° C. The reaction time ranges from about 5 minutes to 100 hours, preferably from about 1 to 5 hours.

The hydrolysis of the compound (V) can be carried out by acid hydrolysis or alkali hydrolysis reaction. This hydrolysis reaction process may include a deprotection step.

In the case of alkali hydrolysis, the compound (V) is allowed to react with an alkali (e.g. hydroxide of an inorganic base such as lithium hydroxide, sodium hydroxide, potassium hydroxide and barium hydroxide) in a solvent (e.g. water, alcohols, ethers, or a mixture of two or more of them). As the solvent, a mixture solvent of water-methanol is preferable. As the alkali, sodium hydroxide is preferable.

The amount of the alkali ranges from about 2 to 100, preferably from about 5 to 10 equivalents, relative to the compound (V).

The reaction temperature ranges from about 10° C. to 120° C., preferably from about 50° C. to 120° C. The reaction time ranges from about 5 minutes to 100 hours, preferably from about 10 to 50 hours. The preferred reaction parameters are as follows. The solvent is water-methanol, the reaction temperature is about 50° C. to 120° C., and the reaction time is about 10 to 50 hours.

For acid hydrolysis, the compound (V) is stirred for 0.5 to 18 hours at temperatures ranging from room temperature to 120° C. in the presence of an excess volume of diluted hydrochloric acid alone or in the co-presence of diluted hydrochloric acid and acetic acid.

Most of the compounds (III) are readily available form commercial sources, and can be readily synthesized by the method described in Chemical Abstracts, Vol. 64, p.2026 (1966). Further, when either $Ar^1$ or $Ar^2$ is 2-pyridyl, 2-benzothiazolyl, 2-quinolyl or 2-thiazolyl, the respectively corresponding 2-bromopyridine, 2-chlorobenzothiazole, 2-chloroquinolyl or 2-bromothiazole is allowed to react with a compound represented by the formula:

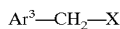

$Ar^3$—$CH_2$—X wherein $Ar^3$ represents an optionally substituted aromatic group and X is of the same meaning as defined above, in the presence of a base to provide the compound (III).

The "optionally substituted aromatic group" shown by $Ar^3$ includes the optionally substituted aromatic group shown by $Ar^1$ or $Ar^2$.

The base mentioned above includes, for example, the above-described strong base.

The amount of the base to be used ranges from about 1 to 5, preferably from about 1 to 3, equivalents relative to the compound (V).

The solvent to be employed for the reaction can be, for example, the above-described alcohols, ethers, halogenated hydrocarbons, aromatic hydrocarbons, nitrites, acid amides, ketones and sulfoxides each alone or in a mixture of two or more species. Among others, THF, ethyl ether, acetonitrile and N,N-dimethylformamide are preferable.

The reaction temperature ranges from about 0° C. to 100° C., preferably from about 10° C. to 50° C. The reaction time ranges from about 5 minutes to 100 hours, preferably from about 1 to 5 hours.

The compound (IV) can be produced by a per se known method, for example, the method described in the above-mentioned Bulletin de la Societe Chimique France, pp.1345–1350 (1956) or an analogous method thereto.

In the above-mentioned respective reactions of this invention and the respective reactions for synthesizing the starting compounds, wherein any of the starting compounds contains an amino group, a carboxyl group or a hydroxyl group, such groups may optionally be protected beforehand using protective groups which are conventionally used in, for example, the field of peptide chemistry, and the respective object compounds can be obtained by removing the protective groups, upon necessity, after the respective synthetic reactions.

The amino-protecting group includes, for example, a $C_{1-6}$ alkylcarbonyl group (e.g. formyl, acetyl and ethylcarbonyl), a $C_{1-6}$ alkyloxycarbonyl group (e.g. methoxycarbonyl and ethoxycarbonyl), benzoyl group, a $C_{7-10}$ aralkylcarbonyl group (e.g. benzylcarbonyl), trityl group, phthaloyl group and N,N-dimethyl aminomethylene group. Each of these groups may optionally have 1 to 3 substituents selected from halogen atoms (e.g. fluorine, chlorine, bromine and iodine) and nitro group.

The carboxyl-protecting group includes, for example, a $C_{1-6}$ alkyl group (e.g. methyl, ethyl, n-propyl, isopropyl, butyl and tert-butyl), phenyl group, trityl group and silyl group. Each of these groups may optionally have 1 to 3 substituents selected from halogen atoms (e.g. fluorine, chlorine, bromine and iodine), a $C_{1-6}$ alkylcarbonyl group (e.g. formyl, acetyl, propionyl and butylcarbonyl) and nitro group.

The hydroxyl-protecting group includes, for example, a $C_{1-6}$ alkyl group (e.g. methyl, ethyl, n-propyl, isopropyl, butyl and tert-butyl), phenyl group, a $C_{7-10}$ aralkyl group (e.g. benzyl), a $C_{1-6}$ alkylcarbonyl group (e.g. formyl, acetyl and propionyl), benzoyl group, $C_{7-10}$ aralkylcarbonyl group (e.g. benzylcarbonyl), tetrahydropyranyl group, tetrahydrofuranyl group and silyl group. Each of these groups may optionally have 1 to 3 substituents selected from halogen atoms (e.g. fluorine, chlorine, bromine and iodine), a $C_{1-6}$ alkyl group (e.g. methyl, ethyl and n-propyl), phenyl group, a $C_{7-10}$ aralkyl group (e.g. benzyl) and nitro.

And, as the method of removing these protective groups, use is made of a method analogous to the method exemplified by procedures using an acid or a base, a reductive deprotection method, or a method utilizing UV light or a chemical reagent such as hydrazine, phenylhydrazine, sodium N-methyl dithiocarbamate, tetrabutylammonium fluoride and palladium acetate.

The compound (I) of this invention can be isolated and purified by a known procedure such as solvent-extraction, pH adjustment, phasic transfer, crystallization, recrystallization and chromatography and so forth. And, while the starting compounds for the compound (I) can also be isolated and purified by substantially the same known procedures as above, the respective reaction mixtures containing them can be directly subjected, omitting the isolation procedure, to the subsequent reaction step.

Where the compound (I) of this invention include optical isomers, stereoisomers, position isomers and rotational isomers, such isomers also fall within the scope of the present invention, which can be obtained respectively as simple substances by synthetic or fractionating procedure.

For example, where the compound of this invention contains optical isomers, such isomers isolated by optical resolution also included in the present invention.

Optical isomers can be produced by subjecting an optically active synthetic intermediate or a mixture of racemic isomers of the final product to optical resolution in accordance with a conventional procedure to provide the corresponding optical isomer.

For the optical resolution, fractional recrystallization, a chiral column method or a diastereomer method, is employed.

1) Fractional recrystallization

The method which comprises allowing a racemic compound to react with an optically active compound to give the corresponding salt, which is then isolated by fractional recrystallization, followed by, when desired, subjecting the isolated compound to neutralization to provide the free optical isomer.

2) Chiral column method

The method of separating the racemic compound or a salt thereof, which comprises utilizing a column for fractionating optical isomers (chiral column). In the case of liquid column chromatography, for example, a mixture of optical isomers is applied to a chiral column such as ENANTIO-OVM (manufactured by Tosoh Corporation) and eluted with water, a buffer solution (e.g. phosphate buffer) and an organic solvent (e.g. ethanol, methanol and acetonitrile), singly or a suitable mixture of them, to isolate the optical isomers. And, in the case of gas chromatography, a chiral column such as CP-Chirasil-DeX CB (manufactured by G. L. Science) is employed for the fractionation. 3) Diastereomer method The method of obtaining the optical isomer, which comprises allowing a mixture of racemic isomers to react with an optically active reagent to give a mixture of diastereomer, subjecting the mixture to a conventional fractionation procedure (e.g. fractional recrystallization and chromatography) to give a simple substance, then cleaving off the optically active reagent moiety by a chemical treatment e.g. hydrolysis. For example, where the compound of this invention contains a hydroxyl group or a primary or secondary amino group, the compound is subjected to condensation reaction with an optically active organic acid (e.g. MPTA [α-methoxy-α-(trifluoromethyl)phenylacetic acid] and (-)-menthoxyacetic acid) to give respective ester or amide diastereomers. On the other hand, where the compound of this invention has a carboxyl group, the compound is subjected to condensation reaction with an optically active amine or an alcohol reagent to give the respective amide or ester diastereomers. The diastereomers thus obtained can be converted to the original compound by subjecting to acid or basic hydrolysis.

The compound (I) of this invention have several meritorious activities such as cerebral neuronal degeneration antagonizing activity, brain tissue injury neutralizing activity, and inhibitory activity against production of cytokines (e.g. IL-1 β and TNF α) in human macrophages and cerebral cells. Therefore, these compounds are of value as an anti-neurodegenerative agent for mammalian animals (e.g. man, equine, bovine, dog, cat, rat, mouse and monkey) and can fine application in the treatment, prevention or improved prognosis of neurodegeneration-associated functional disorders such as neurodegenerative diseases (e.g. Alzheimer's disease, Parkinson's disease, Down's syndrome, Pick's disease, Creutzfeldt-Jakob diseases, multiple sclerosis and bacterial or viral meningitis such as Borna disease, postvaccination encephalitis and AIDS-associated encephalopathy, etc.), and brain dysfunctions (e.g. cerebral infarction, cerebral hemorrhage, subarachnoid hemorrhage and trauma, etc.).

The compound (I) of this invention are also effective in palliating cytokine-associated symptoms such as general malaise, pyrexia, sleep, headache, arthralgia and anorexia, and mental symptoms such as depression in the above-mentioned mammalian animals.

The compound (I) of this invention have only a low toxic potential and can be safely administered either as they are or in various dosage forms prepared from the compound (I) mixed with a pharmaceutically acceptable carriers, such as tablets (including dragees and film-coated tablets), powdery preparations, granules, capsules (including soft capsules), liquid preparations, injections, suppositories and controlled-release preparations, either orally or non-orally (e.g. local, rectal or intravenous administration). The amount of the compound (I) contained in the pharmaceutical preparations of this invention ranges from 0.1 to nearly 100 weight % based on the total composition. The dosage depends on the subject of administration, the route of administration, the diseases to be treated and other factors. For example, in the case of treating viral meningitis, about 0.1 to 500 mg, preferably about 1 to 100 mg, more preferably about 5 to 100 mg, as the active component can be administered orally for a human adult (60 kg) once or in a few divided doses daily.

The pharmaceutically acceptable carriers that can be used for preparing the compositions of this invention include various organic and inorganic carriers which are conventionally used as materials for preparing pharmaceutical compositions. For example, mention is made of excipients, lubricants, binders and disintegrators in solid compositions; and solvents, solubilizers, suspending agents, isotonizing agents, buffering agents and soothing agents in liquid compositions. And, upon necessity, a variety of additives such as preservatives, antioxidants, coloring agents, sweeteners, adsorbents and wetting agents can also be used.

The excipient includes, for example, lactose, sucrose, D-mannitol, starch, corn starch, crystalline cellulose and light silicic anhydride.

The lubricant includes, for example, magnesium stearate, calcium stearate, talc and colloid silica.

The binder includes, for example, crystalline cellulose, sucrose D-mannitol, dextrin, hydroxypropyl cellulose, hydroxypropylmethyl cellulose, polyvinyl pyrrolidone, starch, sucrose, gelatine, methyl cellulose and sodium carboxymethyl cellulose.

The disintegrator includes, for example, starch, carboxymethyl cellulose, carboxymethyl cellulose calcium, crosscarmellose sodium, carboxymethyl starch sodium and L-hydroxypropyl cellulose.

The solvent includes, for example, water for injection, alcohol, propylene glycol, macrogol, sesame oil and corn oil.

The solubilizer includes, for example, polyethylene glycol, propylene glycol, D-mannitol, benzyl benzoate, ethanol, trisaminomethane, cholesterol, triethanolamine, sodium carbonate and sodium citrate.

The suspending agent includes, for example, a surfactant such as stearyl triethanolamine, sodium lauryl sulfate, lauryl aminopropionic acid, lecithin, benzalkonium chloride, benzethonium chloride and glyceryl monostearate; and hydrophiLic macromolecular substances including polyvinyl alcohol, polyvinyl pyrrolidone, carboxymethyl cellulose sodium, methyl cellulose, hydroxymethyl cellulose, hydroxyethyl cellulose and hydroxypropyl cellulose.

The isotonizing agent includes, for example, glucose, D-sorbitol, sodium chloride, glycerol and D-mannitol.

The buffer agent includes, for example, phosphate, acetate, carbonate and citrate.

The soothing agent includes, for example, benzyl alcohol.

The preservative agent includes, for example, p-hydroxybenzoic acid esters, chlorobutanol, benzyl alcohol, phenethylalcohol, dehydroacetic acid and sorbic acid.

The antioxidant agent includes, for example, sulfite and ascorbic acid.

EXAMPLES

The following reference examples, working examples and experimental examples are further illustrative of the present invention. It should be understood that these examples are merely illustrative and are not intended to limit the scope of this invention, which may optionally be modified without departing from the scope of the present invention.

In the following reference examples and working examples, the term "room temperature" is used to mean temperatures ranging from 0 to 30° C. For drying organic solvents, anhydrous magnesium sulfate or anhydrous sodium sulfate was employed. Unless otherwise specified, "%" means "weight %.".

The other abbreviations used in the description have the following meanings.

s: singlet
d: doublet
t: triplet
q: quartet
m: multiplet
br: broad
J:coupling constant
Hz: Herz
$CDCl_3$: deuterochloroform
THF: tetrahydrofuran
DMF: N,N-dimethylformamide
DMSO: dimethyl sulfoxide
$^1$H-NMR: proton nuclear magnetic resonance (generally measured by using free compound in $CDCl_3$)

Reference Example 1
2-(p-Fluorophenyl)phenylacetonitrile

A solution of p-fluoromandelonitrile (45 g) in benzene (90 g) was added, in limited amounts, to sulfuric acid (85 ml) under stirring at temperatures ranging from 5° to 10° C. The mixture was stirred for further 30 minutes. The reaction mixture was added to water (500 ml), which was subjected to extraction with ethyl acetate (300 ml×2). The extract solution was washed with water, dried over anhydrous sodium sulfate and concentrated to provide the title compound (59.5 g) as a colorless oily product.

Reference Example 2
2-(2-Methoxyphenyl)phenylacetonitrile

In substantially the same procedure as in Reference Example 1, 2-(2-methoxyphenyl)phenylacetonitrile was produced.

Reference Example 3
2,2-Bis(4-methoxyphenyl)acetonitrile

In substantially the same procedure as in Reference Example 1, 2,2-bis(4-methoxyphenyl)acetonitrile was produced.

Reference Example 4
2-(4-Methoxyphenyl)-2-(2-naphthyl)acetonitrile

In substantially the same procedure as in Reference Example 1, 2-(4-methoxyphenyl)-2-(2-naphthyl)acetonitrile was produced.

Reference Example 5
2-(2-Pyridyl)phenylacetonitrile

To a solution of benzylcyanide (12.33 g) in tetrahydrofuran (85 ml) was added dropwise, at −70° C. in argon streams, a hexane solution (65 ml) of n-butyl lithium. The mixture was then stirred for 30 minutes at −50° C., to which was then added dropwise 2-bromopyridine (9.7 ml). The reaction temperature was gradually raised up to 0° C. Fifteen minutes later, a saturated ammonium chloride solution was added to the reaction mixture, which was subjected to extraction with ethyl acetate. The extract solution was washed with water, dried over anhydrous sodium sulfate and concentrated to dryness. The concentrate was purified by means of a silica gel column chromatography to give the title compound (6.59 g).

Reference Example 6
2-(2-Benzothiazolyl)phenylacetonitrile

In tetrahydrofuran (20 ml) was suspended 35% potassium hydride (1.12 g) which was washed with hexane in advance. To the suspension was added dropwise, under ice-cooling, phenylacetonitrile (1 g). The mixture was stirred for 10 minutes, to which was added 2-chlorobenzothiazole (1.45 g). The mixture was stirred for further 15 minutes. The reaction mixture was poured into a saturated aqueous solution of ammonium chloride containing ice pieces. The organic layer was subjected to extraction with ethyl acetate. The extract solution was washed with water, dried over anhydrous sodium sulfate and concentrated to dryness. The concentrate was purified by means of a silica gel column chromatography to give the title compound (1.14 g).

Reference Example 7
2-(2-Quinolyl)phenylacetonitrile

In substantially the same manner as in Reference Example 6, 2-(2-quinolyl)phenylacetonitrile was obtained.

In Table 1, the structural formulae and NMR spectra of the respective compounds produced in Reference Examples 1 to 7 are shown.

TABLE 1

$$\underset{Ar^2}{\overset{Ar^1}{>}}\!\!-CN$$

| Ref. Ex. No. | Ar¹ | Ar² | ¹H-NMR ($\delta_{ppm}$, CDCl₃) |
|---|---|---|---|
| 1 | 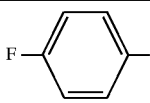 |  | 5.13(1H, s), 7.00–7.50(9H, m) |
| 2 | 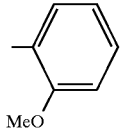 | 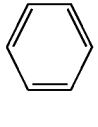 | 3.85(3H, s), 5.55(1H, s), 6.79–7.15(2H, m), 7.22–7.42(7H, m) |
| 3 | 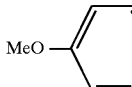 | 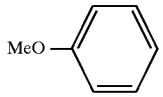 | 3.80(6H, s), 5.05(1H, s), 6.89(4H, d), 7.23(4H, d) |
| 4 | 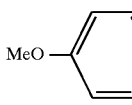 | 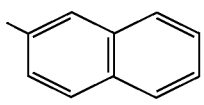 | 3.80(3H, s), 5.27(1H, s), 6.90(2H, d), 7.23–7.39(3H, m), 7.45–7.57(2H, m), 7.75–7.93(4H, m) |
| 5 | 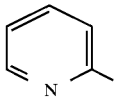 |  | 5.32(1H, s), 7.21–7.30(2H, m), 7.31–7.49(5H, m), 7.66–7.76(1H, m), 8.59–8.63(1H, m) |
| 6 | 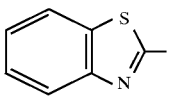 |  | 5.64(1H, s), 7.36–7.60(7H, m), 7.84, 8.08(1H each, ddd) |
| 7 | 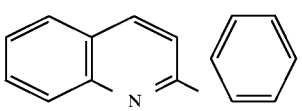 |  | 5.53(1H, s), 7.30–7.62(7H, m), 7.73–7.85(2H, m), 8.10–8.20(2H, m) |

Reference Example 8

Ethyl 7,7-bis(4-methoxyphenyl)-7-cyanoheptanoate

To a solution of bis(4-methoxyphenyl)acetonitrile (1.0 g, 4 mmol) in N,N-dimethylformamide (5 ml) was added 60% oil sodium hydride (0.24 g, 6 mmol) while stirring under ice-cooling. The mixture was stirred for 30 minutes under the same conditions, to which was added, while stirring under ice-cooling, ethyl 6-bromohexanoate (0.89 g, 4 mmol). The mixture was stirred for 2 hours at room temperature, to which was added a saturated aqueous solution of ammonium chloride. The mixture was subjected to extraction with ethyl acetate. The organic layer was washed with water and a saturated aqueous saline solution, which was dried over anhydrous sodium sulfate. The solvent was distilled off under reduced pressure, and the residue was subjected to a silica gel column chromatography, eluting with hexane—ethyl acetate (4:1) to give 1.1 g of the title compound.

Reference Example 9

Ethyl 6-cyano-6,6-diphenylhexanoate

In substantially the same manner as in Reference Example 8, ethyl 6-cyano-6,6-diphenylhexanoate was produced.

Reference Example 10

Ethyl 7-cyano-7,7-diphenylheptanoate

In substantially the same manner as in Reference Example 8, ethyl 7-cyano-7,7-diphenylheptanoate was produced.

Reference Example 11

Ethyl 7-cyano-7-(4-fluorophenyl)-7-phenylheptanoate

In substantially the same manner as in Reference Example 8, ethyl 7-cyano-7-(4-fluorophenyl)-7-phenylheptanoate was produced.

Reference Example 12

Ethyl 7-cyano-7-(2-methoxyphenyl)-7-phenylheptanoate

In substantially the same manner as in Reference Example 8, ethyl 7-cyano-7-(2-methoxyphenyl)-7-phenylheptanoate was produced.

Reference Example 13

Ethyl 7-cyano-7-(4-methoxyphenyl)-7-(2-naphthyl)heptanoate

In substantially the same manner as in Reference Example 8, ethyl 7-cyano-7-(4-methoxyphenyl)-7-(2-naphthyl)heptanoate was produced.

Reference Example 14
Diethyl 2,2-diphenylsuberate

In substantially the same manner as in Reference Example 8, diethyl 2,2-diphenylsuberate was produced.

Reference Example 15
Ethyl 6-cyano-6-phenyl-6-(2-pyridyl)hexanoate

In substantially the same manner as in Reference Example 8, ethyl 6-cyano-6-phenyl-6-(2-pyridyl)hexanoate was produced.

Reference Example 16
Ethyl 7-cyano-7-phenyl-7-(2-pyridyl)heptanoate

In substantially the same manner as in Reference Example 8, ethyl 7-cyano-7-phenyl-(2-pyridyl)heptanoate was produced.

Reference Example 17
Ethyl 6-(2-benzothiazolyl)-6-cyano-6-phenylhexanoate

In substantially the same manner as in Reference Example 8, ethyl 6-(2-benzothiazolyl)-6-cyano-6-phenylhexanoate was produced.

Reference Example 18
Ethyl 7-(2-benzothiazolyl)-7-cyano-7-phenylheptanoate

In substantially the same manner as in Reference Example 8, ethyl 7-(2-benzothiazolyl)-7-cyano-7-phenylheptanoate was produced.

Reference Example 19
Ethyl 7-cyano-7-phenyl-7-(2-quinolyl)heptanoate

In substantially the same manner as in Reference Example 8, ethyl 7-cyano-7-phenyl-7-(2-quinolyl)heptanoate was produced.

In Table 2 and Table 3, the structural formulae and NMR spectra of the respective compounds produced in Reference Examples 8 to 19 are shown.

TABLE 2

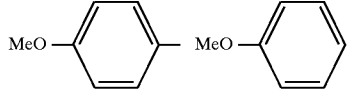

| Ref. Ex. No. | Ar$^1$ | Ar$^2$ | X | Q | $^1$H-NMR ($\delta_{ppm}$, CDCl$_3$) |
|---|---|---|---|---|---|
| 8 | 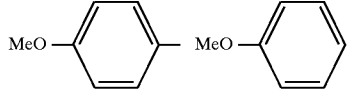 |  | CN | (CH$_2$)$_5$ | 1.24(3H, t), 1.34–1.50(4H, m), 1.52–1.70(2H, m), 2.20–2.34(4H, m), 3.80(6H, s), 4.10(2H, q), 6.86(4H, d), 7.25(4H, d) |
| 9 |  |  | CN | (CH$_2$)$_4$ | 1.22(3H, t), 1.35–1.55(2H, m), 1.61–1.77(2H, m), 2.29(2H, t), 2.35–2.43(2H, m), 4.09(2H, q), 7.25–7.42(10H, m) |
| 10 |  | 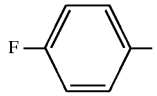 | CN | (CH$_2$)$_5$ | 1.24(3H, t), 1.33–1.53(4H, m), 1.54–1.70(2H, m), 2.26(2H, t), 2.32–2.44(2H, m), 4.11(2H, q), 7.25–7.43(10H, m) |
| 11 |  | 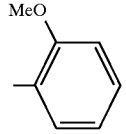 | CN | (CH$_2$)$_5$ | 1.24(3H, t), 1.31–1.50(4H, m), 1.50–1.69(2H, m), 2.22–2.40(4H, m), 4.10(2H, q), 7.04(2H, t), 7.28–7.40(7H, m) |
| 12 |  | 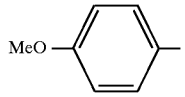 | CN | (CH$_2$)$_5$ | 1.24(3H, t), 1.32–1.49(4H, m), 1.50–1.70(2H, m), 2.18–2.40(3H, m), 2.43–2.61(1H, m), 3.59(3H, s), 4.10(2H, q), 6.86(1H, d), 7.02(1H, dt), 7.18–7.40(6H, m), 7.45(1H, dd) |
| 13 | 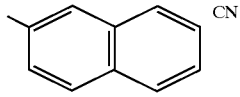 | | CN | (CH$_2$)$_5$ | 1.23(3H, t), 1.31–1.74(6H, m), 2.18–2.50(4H, m), 3.80(3H, s), 4.10(2H, q), 6.87(2H, d), 7.23–7.37(3H, m), 7.44–7.57(2H, m), 7.74–7.98(4H, m) |

TABLE 3

| Ref. Ex. No. | Ar¹ | Ar² | X | Q | ¹H-NMR ($\delta_{ppm}$, CDCl₃) |
|---|---|---|---|---|---|
| 14 | phenyl | phenyl | CO₂Et | (CH₂)₅ | 1.00–1.20(2H, m), 1.15, 1.23(3H each, t), 1.20–1.40(2H, m), 1.45–1.65(2H, m), 2.21(2H, t), 2.30–2.40(2H, m), 4.09, 4.15(2H each, q), 7.20–7.38(10H, m) |
| 15 | 2-pyridyl | phenyl | CN | (CH₂)₄ | 1.21(3H, t), 1.38–1.54(2H, m), 1.61–1.80(2H, m), 2.29(2H, t), 2.35–2.53(1H, m), 2.62–2.79(1H, m), 4.09(2H, q), 7.18–7.40(4H, m), 7.44–7.53(3H, m), 7.62–7.72(1H, m), 8.59–8.66(1H, m) |
| 16 | 2-pyridyl | phenyl | CN | (CH₂)₅ | 1.24(3H, t), 1.30–1.55(4H, m), 1.54–1.70(2H, m), 2.26(2H, t), 2.33–2.51(1H, m), 2.60–2.77(1H, m), 4.11(2H, q), 7.18–7.40(4H, m), 7.44–7.54(3H, m), 7.62–7.72(1H, m), 8.60–8.66(1H, m) |
| 17 | 2-benzothiazolyl | phenyl | CN | (CH₂)₄ | 1.21(3H, t), 1.35–1.82(4H, m), 2.31(2H, t), 2.48–2.65(1H, m), 2.75–2.91(1H, m), 4.09(2H, q), 7.35–7.63(7H, m), 7.82, 8.09(1H each, dd) |
| 18 | 2-benzothiazolyl | phenyl | CN | (CH₂)₅ | 1.24(3H, t), 1.35–1.55(2H, m), 1.53–1.72(2H, m), 2.27(2H, t), 2.46–2.62(1H, m), 2.73–2.89(1H, m), 4.11(2H, q), 7.35–7.65(7H, m), 7.80–7.87(1H, m), 8.07–8.12(1H, m) |
| 19 | 2-quinolyl | phenyl | CN | (CH₂)₅ | 1.24(3H, t), 1.30–1.72(6H, m), 2.28(2H, t), 2.43–2.61(1H, m), 2.78–2.96(1H, m), 4.11(2H, q), 7.21–7.42(3H, m), 7.43–7.61(4H, m), 7.70–7.83(2H, m), 8.05–8.20(2H, m) |

Reference Example 20
2,2-Bis(4-methylphenyl)acetonitrile

In substantially the same manner as in Reference Example 1, 2,2-bis(4-methylphenyl)acetonitrile was produced.

Reference Example 21
2,2-Bis(4-fluorophenyl)acetonitrile

In substantially the same manner as in Reference Example 1, 2,2-bis(4-fluorophenyl)acetonitrile was produced.

Reference Example 22
2-(2-Thiazolyl)phenylacetonitrile

In substantially the same manner as in Reference Example 5, 2-(2-thiazolyl)phenylacetonitrile was produced.

Reference Example 23
2-(2-Quinolyl)-2-(4-methoxyphenyl)acetonitrile

In substantially the same manner as in Reference Example, 2-(2-quinolyl)-2-(4-methoxyphenyl)acetonitrile was produced.

Reference Example 24
2-(2-Quinolyl)-2-(2-naphthyl)acetonitrile

In substantially the same manner as in Reference Example 5, 2-(2-quinolyl)-2-(2-naphthyl)acetonitrile was produced.

Reference Example 25
2-(2-Quinolyl)-2-(2-thienyl)acetonitrile

In substantially the same manner as in Reference Example 5, 2-(2-quinolyl)-2-(2-thienyl)acetonitrile was produced.

In Table 4 are shown structural formulae and NMR spectral data of the respective compounds produced in Reference Examples 20 to 25.

TABLE 4

$$\text{Ar}^1\text{–CH(CN)–Ar}^2$$

| Ref. Ex. No. | Ar¹ | Ar² | ¹H-NMR ($\delta_{ppm}$, CDCl₃) |
|---|---|---|---|
| 20 | 4-Me-C₆H₄ | 4-Me-C₆H₄ | 2.33(6H, s), 5.06(1H, s), 7.13–7.25(8H, m) |

TABLE 4-continued $$\underset{Ar^2}{\overset{Ar^1}{>}}C-CN$$

| Ref. Ex. No. | Ar¹ | Ar² | ¹H-NMR ($\delta_{ppm}$, CDCl₃) |
|---|---|---|---|
| 21 | 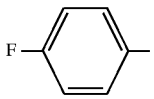 | 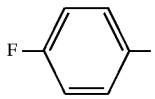 | 5.12(1H, s), 7.07(4H, t), 7.20–7.38(4H, m) |
| 22 |  |  | 5.57(1H, s), 7.36, 7.80(1H each, d), 7.38–7.55(5H, m) |
| 23 | 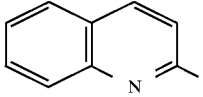 | 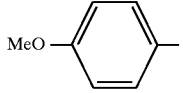 | 3.79(3H, s), 5.46(1H, s), 6.89. 7.42(2H each, d), 7.42, 7.74(1H each, d), 7.57, 7.79(1H each, t), 8.12, 8.15(1H each, d) |
| 24 | 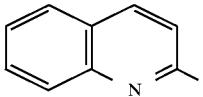 | 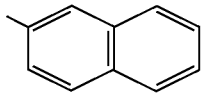 | 5.68(1H, s), 7.40–8.20(13H, m) |
| 25 | 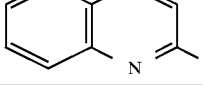 |  | 5.73(1H, s), 6.89–7.40(6H, m), 7.61, 8.12(1H each, d), 7.82(1H, t) |

Reference Example 26
Ethyl 7-cyano-7-phenyl-7-(2-thiazolyl)heptanoate

In substantially the same manner as in Reference Example 8, ethyl 7-cyano-7-phenyl-(2-thiazolyl)heptanoate was produced.

Reference Example 27
Ethyl 7-cyano-7-(4-methoxyphenyl)-7-(2-quinolyl)heptanoate In substantially the same manner as in Reference Example 8, ethyl 7-cyano-7-(4-methoxyphenyl)-7-(2-quinolyl)heptanoate was produced.

Reference Example 28
Ethyl 7-cyano-7-(2-naphthyl)-7-(2-quinolyl)heptanoate

In substantially the same manner as in Reference Example 8, ethyl 7-cyano-7-(2-naphthyl-7-(2-quinolyl)heptanoate was produced.

Reference Example 29
Ethyl 7-cyano-7-(2-quinolyl)-7-(2-thienyl)heptanoate

In substantially the same manner as in Reference Example 8, ethyl 7-cyano-7-(2-quinolyl)-7-(2-thienyl)heptanoate was produced.

Reference Example 30
Ethyl B-cyano-8,8-diphenyl octanoate

In substantially the same manner as in Reference Example 8, ethyl 8-cyano-8,8-diphenyl octanoate was produced.

Reference Example 31
Ethyl 8-cyano-8,8-bis(4-methoxyphenyl)octanoate

In substantially the same manner as in Reference Example 8, ethyl 8-cyano-8,8-bis(4-methoxyphenyl)octanoate was produced.

Reference Example 32
Ethyl 7-cyano-7,7-bis(4-methylphenyl)heptanoate

In substantially the same manner as in Reference Example 8, ethyl 7-cyano-7,7-bis(4-methylphenyl)heptanoate was produced.

Reference Example 33

In substantially the same manner as in Reference Example 8, ethyl 7-cyano-7,7-bis(4-fluorophenyl)heptanoate was produced.

Reference Example 34
Ethyl 7-cyano-7,7-bis(4-hydroxyphenyl)heptanoate

To a solution of ethyl 7-cyano-7,7-bis(4-methoxyphenyl) heptanoate (2.0 g, 5 mmol.) in dichloromethane (20 ml) was added dropwise a solution of boron tribromide (5.07 g, 20 mmol.) in dichloromethane (15 ml) while stirring at −70° C. The reaction mixture was warmed up to 5° C. taking 2 hours, to which was added ice-water, followed by extraction with ethyl acetate. The organic layer was washed with a saturated aqueous saline solution and dried over anhydrous sodium sulfate. The solvent was distilled off under reduced pressure, and the residue was subjected to a silica gel column chromatography, eluting with hexane—ethyl acetate (2:1), to afford the title compound (1.7 g).

Reference Example 35
Ethyl 7-cyano-7,7-bis(4-ethoxyphenyl)heptanoate

To a solution of ethyl 7-cyano-7,7-bis(4-hydroxyphenyl) heptanoate (1.7 g, 4.6 mmol.) in N,N-dimethylformamide (20 ml) was added potassium carbonate (2.1 g, 15.2 mmol.). To the mixture was further added a solution of ethyl iodide (1.97 g, 12.6 mmol.) in N,N-dimethylformamide (3 ml), followed by stirring for 3 hours at 45° C. To the reaction mixture was added water, which was subjected to extraction with ethyl acetate. The organic layer was washed with a saturated aqueous saline solution and dried over anhydrous sodium sulfate. The solvent was distilled off under reduced pressure. The residue was subjected to a silica gel column chromatography, eluting with hexane—ethyl acetate (4:1), to afford the title compound (1.9 g).

Reference Example 36
Ethyl 7-cyano-7,7-bis(4-isopropoxyphenyl)heptanoate

In substantially the same manner as in Reference Example 35, ethyl 7-cyano-7,7-bis(4-isopropoxyphenyl)heptanoate was produced.

Reference Example 37
Ethyl 7-cyano-7,7-bis[4-(2,2,2-trifluoroethoxy)phenyl] heptanoate In substantially the same manner as in Reference Example 35, ethyl 7-cyano-7,7-bis[4-(2,2,2-trifluoroethoxy)phenyl] heptanoate was produced.

Reference Example 38
Ethyl (4-cyano-4,4-diphenylbutylthio)acetate 1) 4-Cyano-4, 4-diphenyl butan-1-ol To a solution of ethyl 4-cyano-4,4-diphenyl butanoate (3.0 g, 10.2 mmol.) in ethanol (50 ml) was added a 1N aqueous solution of sodium hydroxide (30 ml). The mixture was stirred for two hours at room temperature. The solvent was distilled off under reduced pressure. To the residue was added 1N HCl to adjust its pH to be in an acid side, followed by extraction with ethyl acetate. The organic layer was washed with a saturated aqueous saline solution and dried over anhydrous sodium sulfate, followed by distilling off the solvent under reduced pressure. The residue was dissolved in THF (15 ml), which was added dropwise, while stirring under ice-cooling, to a suspension of sodium borohydride (0.77 g, 20.4 mmol.) in THF (15 ml). The mixture was stirred for 30 minutes, which was then stirred for two hours at room temperature, to which was added water, followed by extraction with ethyl acetate. The organic layer was washed with a saturated aqueous saline solution and dilute aqueous solution of sodium thiosulfate, followed by drying over anhydrous sodium sulfate. The solvent was distilled off under reduced pressure. The residue was subjected to a silica gel column chromatography, eluting with hexane—ethyl acetate (1:1) to afford the title compound (1.8 g).

$^1$H-NMR ($\delta$, CDCl$_3$): 1.53–1.83(3H,m), 2.40–2.58(2H, m), 3.70(2H,t), 7.22–7.46(10H,m)

2) 4-Cyano-4,4-diphenyl iodobutane

To a solution of 4-cyano-4,4-diphenylbutan-1-ol (2.2 g, 8.7 mmol.) and pyridine (2.69 ml, 33 mmol.) in acetonitrile (20 ml) was added p-toluenesulfonyl chloride (1.66 g, 8.7 mmol.). To the mixture was added 4-dimethylaminopyridine (a catalytic amount), and the mixture was stirred for two hours at room temperature. To the reaction mixture was added ethyl acetate, which was washed with a 1N HCl and a saturated aqueous saline solution, and, then, dried over anhydrous sodium sulfate. The solvent was distilled off under reduced pressure. The residue was dissolved in acetone (30 ml), to which was added sodium iodide (1.96 g, 13 mmol.). The mixture was refluxed for one hour. The solvent was distilled off under reduced pressure. To the residue was added water, which was subjected to extraction with ethyl acetate. The organic layer was washed with a saturated aqueous saline solution and a dilute aqueous solution of sodium thiosulfate, followed by drying over anhydrous sodium sulfate. The solvent was distilled off under reduced pressure. The residue was subjected to a silica gel column chromatography, eluting with ethyl acetate, to afford the title compound (1.3 g).

H-NMR (8, CDCl$_3$): 1.86–2.04(2H,m), 2.46–2.59(2H,m), 3.21(2H,t), 7.25–7.46(10H,m)

3) Ethyl (4-cyano-4,4-diphenylbutylthio)acetate

To a solution of 4-cyano-4,4-diphenyl iodobutane (0.4 g, 1.1 mmol.) in N,N-dimethylformamide (3 ml) were added potassium carbonate (0.31 g, 2,2 mmol.) and ethyl thioglycolate (0.14 g, 1.2 mmol.). The mixture was stirred for 15 hours at room temperature. To the reaction mixture was added water, which was subjected to extraction with ethyl acetate. The organic layer was washed with a saturated aqueous saline solution and dried over anhydrous sodium sulfate. The solvent was distilled off under reduced pressure. The residue was subjected to a silica gel column chromatography, eluting with hexane - ethyl acetate (4:1) to afford the title compound (0.22 g).

In Tables 5 to 7, are shown structural formulae and NMR spectral data of the respective compounds produced in Reference Examples 26 to 38.

TABLE 5

Ar$^1$\
      >—Q—CO$_2$CH$_2$CH$_3$\
Ar$^2$  X

| Ref. Ex. No. | Ar$^1$ | Ar$^2$ | X | Q | $^1$H-NMR ($\delta_{ppm}$, CDCl$_3$) |
|---|---|---|---|---|---|
| 26 | (thiazole) | (phenyl) | CN | (CH$_2$)$_5$ | 1.24(3H, t), 1.30–1.70(6H, m), 2.26(2H, t), 2.35–2.54(1H, m), 2.61–2.80(1H, m), 4.10(2H, q), 7.33, 7.79(1H each, d), 7.32–7.47(3H, m), 7.48–7.59(2H, m) |
| 27 | (quinoline) | MeO—(phenyl) | CN | (CH$_2$)$_5$ | 1.24(3H, t), 1.33–1.72(6H, m), 2.28(2H, t), 2.41–2.56(1H, m), 2.72–2.90(1H, m), 3.77(3H, s), 4.11(2H, q), 6.84, 7.40(2H each, d),7.47, 7.79(1H each, d), 7.55, 7.75(1H each, t), 8.09, 8.15(1H each, d) |
| 28 | (naphthyl) | (quinoline) | CN | (CH$_2$)$_5$ | 1.22(3H, t), 1.32–1.74(6H, m), 2.27(2H, t), 2.57–2.74(1H, m), 2.85–3.04(1H, m), 4.09(2H, q), 7.41–7.61(5H, m), 7.70–7.91(5H, m), 7.83–8.22(3H, m) |

TABLE 5-continued

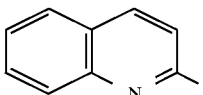

| Ref. Ex. No. | Ar¹ | Ar² | X | Q | ¹H-NMR ($\delta_{ppm}$, CDCl$_3$) |
|---|---|---|---|---|---|
| 29 | 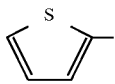 |  | CN | (CH$_2$)$_5$ | 1.23(3H, t), 1.30–1.72(6H, m), 2.26(2H, t), 2.45–2.67(1H, m), 2.70–2.90(1H, m), 4.10(2H, q), 6.94(1H, t), 7.2–7.30(2H, m), 7.53–7.75(2H, m), 7.65, 8.17(1H each, d), 7.80(1H, t) |
| 30 |  |  | CN | (CH$_2$)$_6$ | 1.18–1.70(11H, m), 2.20–2.42(4H, m), 4.11(2H, q), 7.23–7.43(10H, m) |

TABLE 6

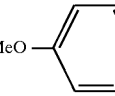

| Ref. Ex. No. | Ar¹ | Ar² | X | Q | ¹H-NMR ($\delta_{ppm}$, CDCl$_3$) |
|---|---|---|---|---|---|
| 31 |  | 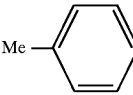 | CN | (CH$_2$)$_5$ | 1.19–1.64(11H, m), 2.20–2.33(4H, m), 3.79(6H, s), 4.11(2H, q), 6.82–6.92(4H, m), 7.22–7.30(4H, m) |
| 32 |  | 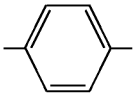 | CN | (CH$_2$)$_5$ | 1.24(3H, t), 1.30–1.69(6H, m), 2.20–2.36(10H, m), 4.10(2H, q), 7.13(4H, d), 7.24(4H, d) |
| 33 |  | 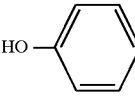 | CN | (CH$_2$)$_5$ | 1.24(3H, t), 1.29–1.70(6H, m), 2.20–2.38(4H, m), 4.01(2H, q), 7.05(4H, t), 7.22–7.38(4H, m) |
| 34 |  | 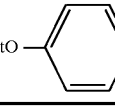 | CN | (CH$_2$)$_5$ | 1.20–1.70(9H, m), 2.17–2.38(4H, m), 4.12(2H, q), 5.79(2H, s), 6.80(4H, d), 7.18(4H, d) |
| 35 | 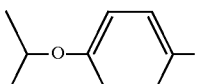 | 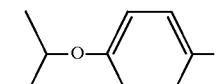 | CN | (CH$_2$)$_5$ | 1.24(3H, t), 1.33–1.70(12H, m). 2.20–2.35(4H, m), 3.95–4.17(6H, m), 6.85(4H, d), 7.25(4H, d) |

TABLE 7

| Ref. Ex. No. | Ar¹ | Ar² | X | Q | ¹H-NMR ($\delta_{ppm}$, CDCl$_3$) |
|---|---|---|---|---|---|
| 36 | | | CN | (CH$_2$)$_5$ | 1.18–1.70(21H, m), 2.19–2.34(4H, m), 4.11(2H, q), 4.42–4.63(2H, m), 6.84(4H, d), 7.24(4H, d) |

TABLE 7-continued $$\underset{Ar^2}{\overset{Ar^1}{>}}\!\!-\!\!\underset{X}{\overset{}{\text{C}}}\!\!-\!\!Q\!-\!CO_2CH_2CH_3$$

| Ref. Ex. No. | Ar¹ | Ar² | X | Q | ¹H-NMR ($\delta_{ppm}$, CDCl₃) |
|---|---|---|---|---|---|
| 37 |  CF₃CH₂O— |  CF₃CH₂O— | CN | (CH₂)₅ | 1.24(3H, t), 1.30–1.70(6H, m), 2.18–2.37(4H, m), 4.11(2H, q), 4.35(4H, q), 6.92(4H, d), 7.30(4H, d) |
| 38 |  |  | CN | (CH₂)₃SCH₂ | 1.26(3H, t), 1.66–1.84(2H, m), 2.43–2.57(2H, m), 2.63–2.75(2H, m), 3.13(2H, s), 4.16(2H, q), 7.23, 7.44(10H, m) |

Working Example 1

7-Cyano-7,7-diphenylheptanohydroxamic acid (Compound 1)

To a solution of hydroxylamine (38.5 g, 0.55 mol) in methanol (300 ml) was added a solution of 28% sodium methylate in methanol (165 ml, 0.83 mol). To the mixture was added, while stirring under ice-cooling, a solution of ethyl 7-cyano-7,7-diphenylheptanoate (18.7 g, 0.055 mol) in methanol (50 ml). The mixture was stirred for 1.5 hour. After completion of the reaction, pH of the reaction mixture was made acidic with 1N HCl. The reaction mixture was subjected to extraction with ethyl acetate. The organic layer was washed with water and a saturated aqueous saline solution, followed by drying over anhydrous sodium sulfate. The solvent was distilled off under reduced pressure, and the residue was crystallized from ethyl acetate—hexane to give 15.2 g of the title compound.

Working Example 2

In substantially the same manner as in Working Example 1, the following compounds 2 to 12 were produced.
Compound 2: 6-cyano-6,6-diphenylhexanohydroxamic acid
Compound 3: 7-cyano-7-(4-fluorophenyl)-7-phenylheptanohydroxamic acid
Compound 4: 7-cyano-7-(2-methoxyphenyl)-7-phenylheptanohydroxamic acid
Compound 5: 7,7-bis(4-methoxyphenyl)-7-cyanoheptanohydroxamic acid
Compound 6: 7-cyano-7-(4-methoxyphenyl)-7-(2-naphthyl)heptanohydroxamic acid
Compound 7: 7,7-diphenyl-7-ethoxycarbonylheptanohydroxamic acid
Compound 8: 6-cyano-6-phenyl-6-(2-pyridyl)hexanohydroxamic acid
Compound 9: 7-cyano-7-phenyl-7-(2-pyridyl)heptanohydroxamic acid
Compound 10: 6-(2-benzothiazolyl)-6-cyano-6-phenylhexanohydroxamic acid
Compound 11: 7-(2-benzothiazolyl)-7-cyano-7-phenylheptanohydroxamic acid
Compound 12: 7-cyano-7-phenyl-7-(2-quinolyl)heptanohydroxamic acid Working Example 3

O-Propionyl-7-cyano-7,7-diphenylheptanohydroxamic acid (Compound 13)

To a solution of 7-cyano-7,7-diphenylheptanohydroxamic acid (4.0 g, 12.4 mmol) and triethylamine (2.5 g, 25 mmol) in tetrahydrofuran (80 ml) was added, while stirring under ice-cooling, propionyl chloride (1.15 g, 12.4 mmol). The mixture was stirred for 30 minutes. After completion of the reaction, the reaction mixture was concentrated under reduced pressure. The concentrate was dissolved in ethyl acetate, which was washed with 0.5N HCl and a saturated aqueous saline solution, followed by drying over anhydrous sodium sulfate. The solvent was distilled off under reduced pressure, and the residue was crystallized from ethyl acetate—hexane to give 4.2 g of the titled compound.

Working Example 4

In substantially the same manner as in Working Example 3, the following compounds 14 to 21 were produced.
Compound 14: O-benzoyl-7-cyano-7,7-diphenylheptanohydroxamic acid
Compound 15: O-propionyl-7-cyano-7-(4-fluorophenyl)-7-phenylheptanohydroxamic acid
Compound 16: O-propionyl-7,7-diphenyl-7-ethoxycarbonylheptanohydroxamic acid
Compound 17: O-benzoyl-7,7-diphenyl-7-ethoxycarbonylheptanohydroxamic acid
Compound 18: O-propionyl-7-cyano-7-phenyl-7-(2-pyridyl)heptanohydroxamic acid
Compound 19: O-benzoyl-7-cyano-7-phenyl-7-(2-pyridyl)heptanohydroxamic acid
Compound 20: O-propionyl-7-cyano-7-phenyl-7-(2-quinolyl)heptanohydroxamic acid
Compound 21: O-benzoyl-7-cyano-7-phenyl-7-(2-quinolyl)heptanohydroxamic acid Working Example 5

O-Ethylcarbamoyl-7-cyano-7,7-diphenylheptanohydroxamic acid (Compound 22)

To a solution of 7-cyano-7,7-diphenylheptanohydroxamic acid (0.32 g, 1 mmol) in tetrahydrofuran (5 ml) was added, while stirring at room temperature, ethyl isocyanate (0.07 g, 1.05 mmol). The mixture was stirred for two hours. After completion of the reaction, the reaction mixture was concentrated under reduced pressure. The concentrate was subjected to a silica gel column chromatography, eluting with hexane - ethyl acetate (1:1), to give 0.2 g of the title compound.

Working Example 6

In substantially the same manner as in Working Example 5, the following compounds 23 and 24 were produced.
Compound 23: O-phenylcarbamoyl-7-cyano-7,7-diphenylheptanohydroxamic acid Compound 24: O-ethylcarbamoyl-7,7-diphenyl-7-ethoxycarbonylheptanohydroxamic acid

Working Example 7

1) In substantially the same manner as in Working Example 1, the following compounds 25 to 37 were produced. (In the parentheses after the compound name, the corresponding starting compound is mentioned.)

Compound 25: 7-cyano-7-phenyl-7-(2-thiazolyl)heptanohydroxamic acid (starting compound: Reference Example 26)

Compound 26: 7-cyano-7-(4-methoxyphenyl)-7-(2-quinolyl)heptanohydroxamic acid (starting compound: Reference Example 27)

Compound 27: 7-cyano-7-(2-naphthyl)-7-(2-quinolyl)heptanohydroxamic acid (starting compound: Reference Example 28)

Compound 28: 7-cyano-7-(2-quinolyl)-7-(2-thienyl)heptanohydroxamic acid (starting compound: Reference Example 29)

Compound 29: 8-cyano-8,8-diphenyloctanohydroxamic acid (starting compound: Reference Example 30)

Compound 30: 8-cyano-8,8-bis(4-methoxyphenyl)octanohydroxamic acid (starting compound: Reference Example 31)

Compound 31: 7-cyano-7,7-bis(4-methylphenyl)heptanohydroxamic acid (starting compound: Reference Example 32)

Compound 32: 7-cyano-7,7-bis(4-fluorophenyl)heptanohydroxamic acid (starting compound: Reference Example 33)

Compound 33: 7-cyano-7,7-bis(4-hydroxyphenyl)heptanohydroxamic acid (starting compound: Reference Example 34)

Compound 34: 7-cyano-7,7-bis(4-ethoxyphenyl)heptanohydroxamic acid (starting compound: Reference Example 35)

Compound 35: 7-cyano-7,7-bis(4-isopropoxyphenyl)heptanohydroxamic acid (starting compound: Reference Example 36)

Compound 36: 7-cyano-7,7-bis[4-(2,2,2-trifluoroethoxy)phenyl]heptanohydroxamic acid (starting compound: Reference Example 37)

Compound 37: 4-cyano-4,4-diphenylbutylthioacetohydroxamic acid (starting compound: Reference Example 38)

2) Compound 32: 7-cyano-7,7-bis(4-fluorophenyl)heptanohydroxamic acid

A methanol solution (100 ml) of ethyl 7-cyano-7,7-bis(4-fluorophenyl)heptanoate (18.5 g) was added to a methanol solution (225 ml) of hydroxylamine hydrochloride (34.61 g) and 28% sodium methylate (150 ml). The mixture was stirred for two hours at room temperature. To the reaction mixture was added 1N HCl to adjust the pH to 2, which was subjected to extraction with ethyl acetate. The organic layer was washed with a saturated aqueous saline solution, dried and concentrated under reduced pressure. The concentrate was subjected to a silica gel column chromatography, eluting with ethyl acetate (1:2), followed by recrystallization from hexane/ethyl acetate to afford the title compound (15.3 g).

3) Compound 34: 7-cyano-7,7-bis(4-ethoxyphenyl)heptanohydroxamic acid (Reference Example 35)

A methanol solution of ethyl 7-cyano-7,7-bis(4-ethoxyphenyl)heptanoate (2.3 g) produced in Reference Example 35 was added to a methanol solution (50 ml) of hydroxylamine hydrochloride (3.51 g) and 28% sodium methylate (16 ml). The mixture was stirred for two hours at room temperature. To the reaction mixture was added 1N HCl to adjust the pH to 2, which was subjected to extraction with ethyl. acetate. The organic layer was washed with a saturated aqueous saline solution, dried and, then, concentrated under reduced pressure. The concentrate was subjected to a silica gel column chromatography, eluting with ethyl acetate, to afford the title compound (1.67 g).

4) Compound 36: 7-cyano-7,7-bis[4-(2,2,2-trifluoroethoxy)phenyl]heptanohydroxamic acid A methanol solution of ethyl 7-cyano-7,7-bis[4-(2,2,2-trifluoroethoxy)phenyl]heptanoate (1.5 g) was added a methanol solution (50 ml) of hydroxylamine hydrochloride (1.96 g) and 28% sodium methylate (11 ml). The mixture was stirred for two hours at room temperature. To the reaction mixture was added iN HCl to adjust the pH to 2, which was subjected to extraction with ethyl acetate. The organic layer was washed with a saturated aqueous saline solution, dried and, then, concentrated under reduced pressure. The concentrate was subjected to a silica gel column chromatography, eluting with hexane/ethyl acetate (1:2) to afford the title compound (0.85 g).

Working Example 8

In substantially the same manner as in Working Example 4, the following compounds 38 to 55 were produced.

Compound 38: 0-propionyl-7-cyano-7-phenyl-7-(2-thiazolyl)heptanohydroxamic acid

Compound 39: O-benzoyl-7-cyano-7-phenyl-7-(2-thiazolyl)heptanohydroxamic acid

Compound 40: O-propionyl-7-cyano-7-(4-methoxyphenyl)-7-(2-quinolyl)heptanohydroxamic acid Compound 41: 0-benzoyl-7-cyano-7-(4-methoxyphenyl)-7-(2-quinolyl)heptanohydroxamic acid Compound 42: 0-propionyl-7-cyano-7-(2-naphthyl)-7-(2-quinolyl)heptanohydroxamic acid Compound 43: 0-benzoyl-7-cyano-7-(2-naphthyl)-7-(2-quinolyl)heptanohydroxamic acid Compound 44: 0-propionyl-7-cyano-7-(2-quinolyl)-7-(2-thienyl)heptanohydroxamic acid Compound 45: 0-benzoyl-7-cyano-7-(2-quinolyl)-7-(2-thienyl)heptanohydroxamic acid Compound 46: 0-propionyl-8-cyano-8,8-diphenyloctanohydroxamic acid Compound 47: 0-benzoyl-8-cyano-8,8-diphenyloctanohydroxamic acid Compound 48: 0-propionyl-7-cyano-7,7-bis(4-methoxyphenyl)heptanohydroxamic acid Compound 49: O-benzoyl-7-cyano-7,7-bis(4-methoxyphenyl)heptanohydroxamic acid Compound 50: O-nicotinoyl-7-cyano-7,7-bis(4-methoxyphenyl)heptanohydroxamic acid Compound 51: O-(4-methoxybenzoyl)-7-cyano-7,7-bis(4-methoxyphenyl)heptanohydroxamic acid Compound 52: O-propionyl-7-cyano-7,7-bis(4-methylphenyl)heptanohydroxamic acid Compound 53: O-benzoyl-7-cyano-7,7-bis(4-methylphenyl)heptanohydroxamic acid Compound 54: O-propionyl-7-cyano-7,7-bis(4-fluorophenyl)heptanohydroxamic acid Compound 55: O-benzoyl-7-cyano-7,7-bis(4-fluorophenyl)heptanohydroxamic acid

Working Example 9

In substantially the same manner as in Working Example 5, the following compound 56 was produced. Compound 56: O-carbamoyl-7-cyano-7,7-bis(4-methoxyphenyl)heptanohydroxamic acid

Working Example 10
8,8,8-Triphenyloctanohydroxamic acid (Compound 57)

1) 3,3,3-triphenylpropanol

To an ethanol solution (300 ml) of 3,3,3-triphenylpropionic acid (15 g) was added dropwise, under ice-cooling, thionyl chloride (5 ml). The mixture was refluxed for 12 hours. The reaction mixture was cooled and concentrated under reduced pressure. The concentrate was dissolved in ethyl acetate, which was washed with water, a saturated aqueous solution of sodium hydrogencarbonate and a saturated aqueous saline solution. The organic layer was dried, which was then concentrated under reduced pressure. The concentrate was dissolved in ether (50 ml), which was added dropwise, under ice-cooling, to an ether suspension (250 ml) of lithium aluminum hydride (1.89 g). The mixture was stirred for one hour at room temperature, which was processed with 10% HCl, followed by addition of ether. The organic layer was washed with water, dried and concentrated under reduced pressure (14.2 g).

2) 3,3,3-Triphenylpropanal To a THF solution (510 ml) of oxalyl chloride (12.5 g) was added dropwise, under argon atmosphere at 70° C., a THF solution (34 ml) of DMSO (10.2 g). The mixture was stirred for 10 minutes, to which was added 3,3,3-triphenyl propanol (14.2 g). The mixture was stirred for one hour at −40° C., to which was added triethylamine (36.4 g). The mixture was stirred for 20 minutes at 0° C. The reaction mixture was diluted with ethyl acetate, which was washed with water, 1N HCl, a saturated aqueous solution of sodium hydrogencarbonate and a saturated aqueous saline solution, followed by drying and concentration under reduced pressure. The concentrate was purified by means of a silica gel column chromatography (hexane:ethyl acetate=10:1), followed by recrystallization from hexane to afford 6.6 g of the title compound, m.p.100°–103° C.

3) Ethyl 8,8,8-triphenyloct-5-enoate

Under ice-cooling, 60% oil sodium hydride (1.68 g) was added to DMSO (42 ml). The mixture was stirred for one hour at 75° C., to which was added a DMSO solution (20 ml) of 4-carboxybutyl triphenylsulphonium bromide (8.87 g). The mixture was stirred for 15 minutes, to which was added a DMSO solution (5 ml) of 3,3,3- triphenyl propanal (2.86 g). The mixture was stirred for 15 minutes, which was poured into 1N HCl and dissolved in ethyl acetate. The solution was washed with water, dried and concentrated under reduced pressure. The concentrate was purified by means of a silica gel column chromatography (hexane:ethyl acetate=4:1), which was dissolved in ethanol (30 ml). To the solution was added dropwise thionyl chloride (5 ml), and the mixture was refluxed for 12 hours. The reaction mixture was cooled and, then, concentrated under reduced pressure. The concentrate was diluted with ethyl acetate, washed with water and concentrated under reduced pressure. The concentrate was purified by means of a silica gel column chromatography (hexane:ethyl acetate=10:1) to afford 6.6 g of the title compound.

4) Ethyl 8,8,8-triphenyloctanoate

To an ethanol solution (6.3 ml) of ethyl 8,8,8-triphenyloct-5-enoate (626 mg) was added 10% Pd-C (188 mg). The mixture was subjected to catalytic hydrogenation for six hours at ambient temperatures under atmospheric pressure. The catalyst was filtered off and the filtrate was concentrated under reduced pressure. The concentrate was purified by means of a silica gel column chromatography (hexane:ethyl acetate=10:1) to afford 620 mg of the title compound.

$^1$N-NMR δ: 1.33(3H,t), 1.00–1.30(8H,m), 2.23(3H,t), 2.26–2.60(2H,m), 4.10(3H,q), 7.13–7.30(15H,m)

5) 8,8,8-Triphenyl octanohydroxamic acid

To ethyl 8,8,8-triphenyl octanoate (3.35 g) was added an ethanol solution of hydroxylamine (1M solution; 58.7 ml). The mixture was stirred for 3 hours at room temperature. The reaction mixture was concentrated under reduced pressure, which was dissolved in ethyl acetate. The solution was washed with 1N HCl and water, dried and concentrated under reduced pressure. Crude crystals thus obtained was recrystallized from hexane/ethyl acetate to give the title compound, m.p.121°–122° C.

Working Example 11

In substantially the same manner as in Working Example 2, the following compounds 58 and 59 were produced by starting from the compound 57. Compound 58: O-propionyl-8, 8, 8-triphenyl octanohydroxamic acid, m.p.115°–117° C.

Compound 59: O-benzoyl-8,8, 8-triphenyl octanohydroxamic acid, m.p.123°–124° C.

Working Example 12
O-ethylcarbamoyl-7-cyano-7,7-[4-(ethylcarbamoyloxy) phenyl] heptanohydroxamic acid (Compound 60)

To a THF solution (10 ml) of 7-cyano-7,7-(4-hydroxyphenyl)heptanohydroxamic acid (0.41 g) was added dropwise ethyl isocyanate (0.5 g). The mixture was stirred for two days at room temperature, to which were added water and ethyl acetate. The organic layer was washed with a saturated aqueous saline solution, dried and concentrated under reduced pressure. The concentrate was purified by means of a silica gel column chromatography (hexane:ethyl acetate=2:1) to afford 600 mg of the title compound.

$^1$N-NMR δ: 1.08(15H,m), 2.20–2.56(4H,m), 3.20–3.44 (6H,m), 4.97–5.10(2H,m), 5.40–5.55(1H,m), 7.12(4H,d), 7.33(4H,d), 8.20–8.33(1H,m)

In Tables 8 to 20, the structural formulae and NMR spectra of the respective compounds 1 to 56 were shown.

TABLE 8

Ar$^1$\
      >—Q—CONH—O—R$^1$\
Ar$^2$/ X

| Cpd. No. | Ar$^1$ | Ar$^2$ | X | Q | R$^1$ | m.p. (°C.) | NMR (δ, CDCl$_3$) |
|---|---|---|---|---|---|---|---|
| 1 | Ph | Ph | CN | (CH$_2$)$_5$ | H | 118–119 | 1.20–1.51(4H, m), 1.51–1.69(2H, m), 2.08(2H, t), 2.34(2H, t), 7.22–7.41(10H, m), 8.40–9.00(1H, br) |

TABLE 8-continued $$\begin{array}{c} Ar^1 \\ \phantom{Ar^2}\diagdown \\ \phantom{Ar^2}\diagup\!\!\!\diagdown Q\!-\!CONH\!-\!O\!-\!R^1 \\ Ar^2\ X \end{array}$$

| Cpd. No. | Ar¹ | Ar² | X | Q | R¹ | m.p. (°C.) | NMR (δ, CDCl₃) |
|---|---|---|---|---|---|---|---|
| 2 | Ph | Ph | CN | (CH₂)₄ | H | 109–110 | 1.32–1.51(2H, m), 1.58–1.75(2H, m), 2.09(2H, t), 2.36(2H, t), 7.21–7.40(10H, m), 8.30–8.70(1H, br) |
| 3 | 4-F-C₆H₄ | Ph | CN | (CH₂)₅ | H | 110–111 | 1.24–1.50(4H, m), 1.51–1.69(2H, m), 2.09(2H, t), 2.23–2.39(2H, m), 7.03(2H, t), 7.22–7.41(7H, m), 8.20–9.20(1H, br) |
| 4 | 2-MeO-C₆H₄ | Ph | CN | (CH₂)₅ | H | Syrup | 1.15–1.68(6H, m), 2.00–2.30(3H, m), 2.41–2.58(1H, m), 3.56(3H, s), 6.86(1H, d), 7.01(1H, dt), 7.17–7.48(7H, m), 8.00–9.10(1H, br) |
| 5 | 4-MeO-C₆H₄ | 4-MeO-C₆H₄ | CN | (CH₂)₅ | H | Syrup | 1.30–1.50(4H, m), 1.52–1.75(2H, m), 2.17(2H, t), 2.20–2.35(2H, m), 3.79(6H, s), 6.86(4H, d), 7.15–7.30(5H, m), 8.15–8.70(1H, br) |

TABLE 9

$$\begin{array}{c} Ar^1 \\ \phantom{Ar^2}\diagdown \\ \phantom{Ar^2}\diagup\!\!\!\diagdown Q\!-\!CONH\!-\!O\!-\!R^1 \\ Ar^2\ X \end{array}$$

| Cpd. No. | Ar¹ | Ar² | X | Q | R¹ | m.p. (°C.) | NMR (δ, CDCl₃) |
|---|---|---|---|---|---|---|---|
| 6 | 4-MeO-C₆H₄ | 2-naphthyl | CN | (CH₂)₅ | H | Amorphoas | 1.23–1.75(6H, m), 2.00–2.19(2H, m), 2.33–2.52(2H, m), 3.79(3H, s), 6.87(2H, d), 7.20–7.36(3H, m), 7.44–7.57(2H, m), 7.70–7.98(4H, m) |
| 7 | Ph | Ph | CO₂C₂H₅ | (CH₂)₅ | H | 102–103 | 0.97–1.15(2H, m), 1.14(3H, t), 1.20–1.36(2H, m), 1.45–1.63(2H, m), 2.02(2H, t), 2.26–2.38(2H, m), 4.14(2H, q), 7.19–7.35(10H, m), 8.20–8.80(1H, br) |
| 8 | 2-pyridyl | Ph | CN | (CH₂)₄ | H | Syrup | 1.32–1.53(2H, m), 1.60–1.80(2H, m), 2.12(2H, t), 2.28–2.47(1H, m), 2.60–2.79(1H, m), 7.20–7.40(4H, m), 7.40–7.52(3H, m), 7.62–7.74(1H, m), 8.59–8.66(1H, m) |
| 9 | 2-pyridyl | Ph | CN | (CH₂)₅ | H | Syrup | 1.28–1.50(4H, m), 1.50–1.70(2H, m), 2.09(2H, t), 2.25–2.48(1H, m), 2.56–2.73(1H, m), 7.19–7.40(4H, m) <7.40–7.51(3H, m), 7.62–7.72(1H, m), 8.59–8.66(1H, m) |

TABLE 10

$$\begin{array}{c} Ar^1 \\ \phantom{Ar^2}\diagdown \\ \phantom{Ar^2}C-Q-CONH-O-R^1 \\ \phantom{Ar^2}\diagup \\ Ar^2\phantom{-}X \end{array}$$

| Cpd. No. | Ar¹ | Ar² | X | Q | R¹ | m.p. (°C.) | NMR (δ, CDCl₃) |
|---|---|---|---|---|---|---|---|
| 10 | benzothiazol-2-yl | Ph | CN | (CH₂)₄ | H | Syrup | 1.30–1.82(4H, m), 2.13(2H, t), 2.40–2.60(1H, m), 2.70–2.89(1H, m), 7.30–7.60(7H, m), 7.80, 8.07(1H each, d), 8.80(1H br) |
| 11 | benzothiazol-2-yl | Ph | CN | (CH₂)₅ | H | Syrup | 1.30–1.72(6H, m), 2.10(2H, t), 2.40–2.59(1H, m), 2.68–2.86(1H, m), 7.30–7.61(7H, m), 7.81, 8.08(1H each, d) |
| 12 | quinolin-2-yl | Ph | CN | (CH₂)₅ | H | Syrup | 1.30–1.72(6H, m), 2.09(2H, t), 2.40–2.58(2H, m), 2.74–2.90(1H, m), 7.24–7.37(3H, m), 7.42–7.60(4H, m), 7.70–7.81(2H, m), 8.09, 8.15(1H each, d), 8.62(1H, br) |
| 13 | Ph | Ph | CN | (CH₂)₅ | COC₂H₅ | Syrup | 1.21(3H, t), 1.31–1.55(4H, m), 1.56–1.77(2H, m), 2.21(2H, t), 2.24–2.41(2H, m), 2.50(2H, q), 7.21–7.48(10H, m), 8.90–9.10(1H, br) |
| 14 | Ph | Ph | CN | (CH₂)₅ | COPh | 97–98 | 1.38–1.58(4H, m), 1.60–1.82(2H, m), 2.21–2.43(4H, m), 7.22–7.57(12H, m), 7.64(1H, t), 8.09(2H, d), 9.03–9.20(1H, br) |

TABLE 11

$$\begin{array}{c} Ar^1 \\ \phantom{Ar^2}\diagdown \\ \phantom{Ar^2}C-Q-CONH-O-R^1 \\ \phantom{Ar^2}\diagup \\ Ar^2\phantom{-}X \end{array}$$

| Cpd. No. | Ar¹ | Ar² | X | Q | R¹ | m.p. (°C.) | NMR (δ, CDCl₃) |
|---|---|---|---|---|---|---|---|
| 15 | 4-F-C₆H₄ | Ph | CN | (CH₂)₅ | COC₂H₅ | 52–53 | 1.22(3H, t), 1.35–1.55(4H, m), 1.56–1.75(2H, m), 2.21(2H, t), 2.27–2.50(2H, m), 2.50(2H, q), 7.04(2H, t), 7.24–7.41(7H, m), 8.75–9.15(1H, br) |
| 16 | Ph | Ph | CO₂C₂H₅ | (CH₂)₅ | COC₂H₅ | Syrup | 0.99–1.16(2H, m), 1.15, 1.22(3H each, t), 1.25–1.41(2H, m), 1.54–1.70(2H, m), 2.15(2H, t), 2.30–2.40(2H, m), 2.50, 4.15(2H each, q), 7.20–7.30.(10H, m), 8.85(1H, brs) |
| 17 | Ph | Ph | CO₂C₂H₅ | (CH₂)₅ | COPh | Syrup | 1.00–1.17(2H, m), 1.15(3H, t), 1.29–1.44(2H, m), 1.58–1.75(2H, m), 2.23(2H, t), 2.30–2.41(2H, m), 4.15(2H, q), 7.21–7.33(10H, m), 7.42–7.52(2H, m), 7.59–7.69(1H, m), 8.06–8.14(2H, m), 9.13(1H, br s) |

TABLE 12

$$\text{Ar}^1\text{-}\underset{\text{Ar}^2\ X}{\text{C}}\text{-}Q\text{-}CONH\text{-}O\text{-}R^1$$

| Cpd. No. | Ar¹ | Ar² | X | Q | R¹ | m.p. (°C.) | NMR (δ; CDCl₃) |
|---|---|---|---|---|---|---|---|
| 18 | 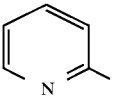 (2-pyridyl) | Ph | CN | (CH₂)₅ | COC₂H₅ | Syrup | 1.22(3H, t), 1.35–1.53(4H, m), 1.60–1.80(2H, m), 2.21(2H, t), 2.33–2.52(1H, m), 2.51(2H, q), 2.59–2.78(1H, m), 7.18–7.40(4H, m), 7.43–7.52(3H, m), 7.62–7.72(1H, m), 8.62(1H, dd), 9.01(1H, br s) |
| 19 | 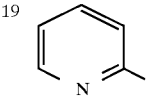 (2-pyridyl) | Ph | CN | (CH₂)₅ | COPh | Syrup | 1.30–1.60(4H, m), 1.60–1.80(2H, m), 2.29(2H, t), 2.30–2.50(1H, m), 2.59–2.80(1H, m), 7.15–7.71(11H, m), 8.00–8.16(2H, m), 8.57–8.66(1H, m), 9.28(1H, br) |
| 20 | 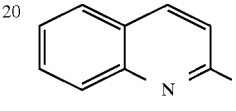 (2-quinolyl) | Ph | CN | (CH₂)₅ | COC₂H₅ | Syrup | 1.22(3H, t), 1.35–1.80(6H, m), 2.23(2H, t), 2.51(2H, q), 2.45–2.60(1H, m), 2.79–2.95(1H, m), 7.26–7.39(3H, m), 745–7.61(4H, m), 7.71–7.82(2H, m), 8.10, 8.16(1H each, d), 8.83(1H br s) |
| 21 | 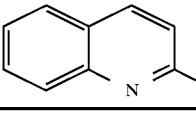 (2-quinolyl) | Ph | CN | (CH₂)₅ | COPh | Syrup | 1.30–1.85(6H, m), 2.31(2H, t), 2.40–2.62(1H, m), 2.75–2.96(1H, m), 7.20–7.82(12H, m), 8.00–8.20(4H, m), 9.12(1H, br s) |

TABLE 13

$$\text{Ar}^1\text{-}\underset{\text{Ar}^2\ X}{\text{C}}\text{-}Q\text{-}CONH\text{-}O\text{-}R^1$$

| Cpd. No. | Ar¹ | Ar² | X | Q | R¹ | m.p. (°C.) | NMR (δ; CDCl₃) |
|---|---|---|---|---|---|---|---|
| 22 | Ph | Ph | CN | (CH₂)₅ | CONHC₂H₅ | Syrup | 1.16(3H, t), 1.33–1.52(4H, m), 1.55–1.75(2H, m), 2.18(2H, t), 2.28–2.42(2H, m), 3.17–3.35(2H, m), 5.55–5.75(1H, br), 7.24–7.42(10H, m), 9.15–9.35(1H, br) |
| 23 | Ph | Ph | CN | (CH₂)₅ | CONHPh | 135–136 | 1.38–1.60(4H, m), 1.60–1.78(2H, m), 2.32–2.46(2H, m), 2.73(2H, t), 7.14(1H, t), 7.21–7.43(12H, m), 7.48(2H, d), 8.22–8.38(1H, br) |
| 24 | Ph | Ph | CO₂C₂H₅ | (CH₂)₄ | CONHC₂H₅ | Syrup | 0.99–1.18(2H, m), 1.15, 1.16(3H each, t), 1.24–1.40(2H, m), 1.52–1.70(2H, m), 2.13(2H, t), 2.30–2.40(2H, m), 3.19–3.34(2H, m), 4.15(2H, q), 5.48(1H, br t), 7.20–7.33(10H, m), 8.96(1H, br s) |

TABLE 14

$$\underset{Ar^2}{\overset{Ar^1}{\diagdown}}\underset{X}{\overset{|}{C}}-Q-CONH-OR^1$$

| Cpd. No. | Ar¹ | Ar² | X | Q | R¹ | m.p.(°C.) | NMR(δ; CDCl₃) |
|---|---|---|---|---|---|---|---|
| 25 |  | Ph | CN | $(CH_2)_5$ | H | Syrup | 1.30–1.70(6H, m), 2.11(2H, t), 2.32–2.51(1H, m), 2.60–2.77(1H, m), 7.34, 7.79(1H each, d), 7.33–7.45(3H, m), 7.46–7.56(2H, m) |
| 26 | 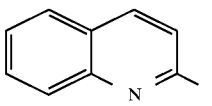 | 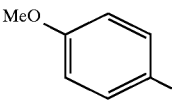 | CN | $(CH_2)_5$ | H | Syrup | 1.30–1.70(6H, m), 2.09(2H, t), 2.36–2.55(1H, m), 2.67–2.86(1H, m), 3.75(3H, s), 6.83, 7.38(2H each, d), 7.43, 7.77(1H each, d), 7.54, 7.74 (1H each, t), 8.07, 8.13(1H each, d), 8.62(1H, br) |
| 27 | 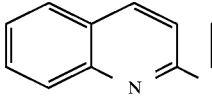 | 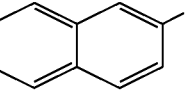 | CN | $(CH_2)_5$ | H | Syrup | 1.20–1.70(6H, m), 2.06(2H, t), 2.50–2.70(1H, m), 2.77–2.98(1H, m), 7.37–7.60(5H, m), 7.68–7.91(5H, m), 8.05, 8.18(1H each, d), 8.09(1H, d), 8.56(1H, br) |
| 28 | 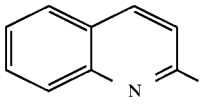 | 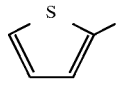 | CN | $(CH_2)_5$ | H | Syrup | 1.25–1.70(6H, m), 2.08(2H, t), 2.40–2.61(1H, m), 2.65–2.85(1H, m), 6.92(1H, t), 7.22 (2H, dd), 7.55(1H, t), 7.60, 8.15(1H each, t), 7.73, 7.78 (1H each, t), 8.14(1H, d), 8.60 (1H, br) |
| 29 | Ph | Ph | CN | $(CH_2)_6$ | H | 93–94 | 1.20–1.50(2H, m), 1.52–1.72 (2H, m), 2.10(2H, t), 2.26–2.40(2H, m), 7.23–7.41(10H, m), 8.00–8.70(1H, m) |

TABLE 15

$$\underset{Ar^2}{\overset{Ar^1}{\diagdown}}\underset{X}{\overset{|}{C}}-Q-CONH-OR^1$$

| Cpd. No. | Ar¹ | Ar² | X | Q | R¹ | m.p. (°C) | NMR (δ; CDCl₃) |
|---|---|---|---|---|---|---|---|
| 30 | MeO– | MeO– | CN | $(CH_2)_6$ | H | 92–93 | 1.20–1.43(6H, m), 1.45–1.64(2H, m), 2.08(2H, t), 2.19–2.32(2H, m), 3.78(6H, s), 6.85(4H, d), 7.25(4H, d), 7.90–8.80(1H, br) |
| 31 | Me– | Me– | CN | $(CH_2)_5$ | H | Syrup | 1.25–1.50(4H, m), 1.50–1.70(2H, m), 2.09(2H, t), 2.23–2.36(8H, m), 7.13(4H, d), 7.23(4H, d), 7.50–8.50(1H, br) |
| 32 | F– | F– | CN | $(CH_2)_5$ | H | 110–111 | 1.22–1.50(4H, m), 1.50–1.72(2H, m), 2.11(2H, t), 2.23–2.37(2H, m), 7.05(4H, t), 7.23–7.39(4H, m), 8.10–8.70(1H, br) |
| 33 | HO– | HO– | CN | $(CH_2)_5$ | H | Amorphoas | 1.27–1.70(6H, m), 2.00–2.30(4H, m), 6.80(4H, d), 7.14(4H, d), 7.37(2H, s), 8.60–8.93(1H, br) |
| 34 | EtO– | EtO– | CN | $(CH_2)_5$ | H | Syrup | 1.27–1.74(12H, m), 2.02–2.33(4H, m), 4.01(4H, q), 6.85(4H, m), 7.24(4H, d), 8.00–8.53(1H, br) |

TABLE 15-continued

Ar¹\
  \\\
   Q—CONH—OR¹\
  /\
Ar² X

| Cpd. No. | Ar¹ | Ar² | X | Q | R¹ | m.p. (°C.) | NMR (δ; CDCl₃) |
|---|---|---|---|---|---|---|---|
| 35 | (CH₃)₂CHO-C₆H₄- | (CH₃)₂CHO-C₆H₄- | CN | (CH₂)₅ | H | Syrup | 1.20–1.72(18H, m), 2.02–2.33(4H, m), 4.40–4.64(2H, m), 6.84(4H, d), 7.23(4H, d), 8.15–8.52(1H, br) |

TABLE 16

Ar¹\
  \\\
   Q—CONH—OR¹\
  /\
Ar² X

| Cpd. No. | Ar¹ | Ar² | X | Q | R¹ | m.p. (°C.) | NMR (δ; CDCl₃) |
|---|---|---|---|---|---|---|---|
| 36 | F₃CCH₂O-C₆H₄- | F₃CCH₂O-C₆H₄- | CN | (CH₂)₅ | H | Syrup | 1.27–1.72(6H, m), 2.03–2.37(4H, m), 4.34(4H, q), 7.29(4H, d), 8.17–8.50(1H, br) |
| 37 | Ph | Ph | CN | (CH₂)₃SCH₂ | H | Syrup | 1.60–1.70(2H, m), 2.37–2.70(4H, m), 3.14(2H, s), 7.20–7.44(10H, m) |
| 38 | thiazol-2-yl | Ph | CN | (CH₂)₅ | COC₂H₅ | Syrup | 1.22(3H, t), 1.30–1.79(6H, m), 2.21(2H, t), 2.36–2.54(1H, m), 2.51(2H, q), 2.62–2.80(1H, m), 7.34, 7.80(1H each, d), 7.30–7.46(3H, m), 7.50–7.58(2H, m), 9.03(1H, br s) |
| 39 | thiazol-2-yl | Ph | CN | (CH₂)₅ | COPh | Syrup | 1.30–1.82(6H, m), 2.29(2H, t), 2.37–2.5(1H, m), 2.63–2.82(1H, m), 7.29–7.70(8H, m), 7.33, 7.80(1H each, d), 8.09(2H, d), 9.21(1H, br s) |
| 40 | quinolin-2-yl | MeO-C₆H₄- | CN | (CH₂)₅ | COC₂H₅ | Syrup | 1.2(3H, t), 1.38–1.80(6H, m), 2.23(2H, t), 2.41–2.57(1H, m), 2.50(2H, q), 2.73–2.90(1H, m), 3.77(3H, s), 6.84, 7.40(2H each, d), 7.46, 7.79(1H each, d), 7.55, 7.75(1H each, t), 8.09, 8.15(1H each, d), 8.82(1H, br s) |

TABLE 17

Ar¹\
  \\\
   Q—CONH—OR¹\
  /\
Ar² X

| Cpd. No. | Ar¹ | Ar² | X | Q | R¹ | m.p. (°C.) | NMR (δ; CDCl₃) |
|---|---|---|---|---|---|---|---|
| 41 | quinolin-2-yl | MeO-C₆H₄- | CN | (CH₂)₅ | COPh | Syrup | 1.40–1.83(6H, m), 2.30(2H, t), 2.41–2.59(1H, m), 2.74–2.91(1H, m), 3.76(3H, s), 6.84, 7.40(2H each, d), 7.42–7.81(7H, m), 8.08(2H, d), 8.08, 8.15(1H each, d), 9.18(1H, br s) |

TABLE 17-continued $$\underset{Ar^2}{\overset{Ar^1}{>}}\underset{X}{\overset{}{\underset{}{\bigg|}}}Q-CONH-OR^1$$

| Cpd. No. | Ar¹ | Ar² | X | Q | R¹ | m.p. (°C.) | NMR (δ; CDCl₃) |
|---|---|---|---|---|---|---|---|
| 42 | quinolin-2-yl | naphthalen-2-yl | CN | (CH₂)₅ | COC₂H₅ | Syrup | 1.20(3H, t), 1.34–1.80(6H, m), 2.22(2H, t), 2.49(2H, q), 2.56–2.72(1H, m), 2.86–3.03(1H, m), 7.39–7.61(5H, m), 7.75, 7.78(2H each, d), 7.88(1H, t), 8.07, 8.20(1H each, d), 8.11(1H, d), 8.85(1H, br s) |
| 43 | quinolin-2-yl | naphthalen-2-yl | CN | (CH₂)₅ | COPh | Syrup | 1.35–1.85(6H, m), 2.30(2H, t), 2.57–2.75(1H, m), 2.87–3.05(1H, m), 7.40–7.69(8H, m), 7.70–7.91(5H, m), 8.03–8.15(4H, m), 8.20(1H, d), 9.12(1H, br s) |
| 44 | quinolin-2-yl | thiophen-2-yl | CN | (CH₂)₅ | COC₂H₅ | Syrup | 1.21(3H, t), 1.35–1.80(6H, m), 2.21(2H, t), 2.49(2H, q), 2.43–2.63(1H, m), 2.70–2.90(1H, m), 6.94(1H, dd), 7.23(2H, dd), 7.56, 7.75(1H each, t), 7.62, 8.16(1H each, d), 7.79(1H, t), 8.16(1H, d), 8.95(1H, br s) |

TABLE 18

$$\underset{Ar^2}{\overset{Ar^1}{>}}\underset{X}{\overset{}{\underset{}{\bigg|}}}Q-CONH-OR^1$$

| Cpd. No. | Ar¹ | Ar² | X | Q | R¹ | m.p. (°C.) | NMR (δ; (CDCl₃) |
|---|---|---|---|---|---|---|---|
| 45 | quinolin-2-yl | thiophen-2-yl | CN | (CH₂)₅ | COPh | Syrup | 1.35–1.82(6H, m), 2.29(2H, t), 2.47–2.67(1H, m), 2.70–2.91(1H, m), 6.94(1H, dd), 7.20–7.28(2H, m), 7.47, 7.59, 7.75(1H each, t), 7.48, 8.16(1H each, d), 7.63(2H, d), 7.79(1H, t), 8.08(2H, d), 8.16(1H, d), 9.18(1H, br s) |
| 46 | Ph | Ph | CN | (CH₂)₆ | COC₂H₅ | Syrup | 1.22(3H, t), 1.25–1.52(6H, m), 1.54–1.72(2H, m), 2.22(2H, t), 2.28–2.32(2H, m), 2.41(2H, q), 7.22–7.41(10H, m), 8.79(1H, br s) |
| 47 | Ph | Ph | CN | (CH₂)₆ | COPh | 96–97 | 1.30–1.53(6H, m), 1.55–1.68(2H, m), 2.20–2.42(4H, m), 7.23–7.54(12H, m), 7.59–7.68(1H, m), 8.00(2H, dd), 9.08(1H, br s) |
| 48 | 4-MeO-C₆H₄ | 4-MeO-C₆H₄ | CN | (CH₂)₅ | COC₂H₅ | Syrup | 1.22(3H, t), 1.35–1.46(4H, m), 1.60–1.70(2H, m), 2.15–2.32(4H, m), 2.50(2H, q), 3.79(6H, s), 6.86(4H, d), 7.25(4H, d), 8.83(1H, br s) |
| 49 | 4-MeO-C₆H₄ | 4-MeO-C₆H₄ | CN | (CH₂)₅ | COPh | Syrup | 1.38–1.53(4H, m), 1.60–1.80(2H, m), 2.24–2.36(4H, m), 3.79(6H, s), 6.85(4H, d), 7.26(4H, d), 7.48(2H, t), 7.59–7.68(1H, m), 8.09(2H, dd), 9.08–9.17(1H, br) |

TABLE 19

$$Ar^1\text{-}C(Ar^2)(X)\text{-}Q\text{-}CONH\text{-}OR^1$$

| Cpd. No. | Ar¹ | Ar² | X | Q | R¹ | m.p. (°C.) | NMR (δ; CDCl₃) |
|---|---|---|---|---|---|---|---|
| 50 | MeO-C₆H₄- | MeO-C₆H₄- | CN | (CH₂)₅ | CO-(2-pyridyl) | Syrup | 1.35–1.58(4H, m), 1.60–1.82(2H, m), 2.24–2.37(4H, m), 3.79(6H, s), 6.86(4H, d), 7.26(4H, d), 7.45(1H, dd), 8.35(1H, dt), 8.83(1H, dd), 9.27(1H, d), 9.63–9.80(1H, br) |
| 51 | MeO-C₆H₄- | MeO-C₆H₄- | CN | (CH₂)₅ | CO-C₆H₄-OMe | Syrup | 1.32–1.50(4H, m), 1.55–1.77(2H, m), 2.20–2.34(4H, m), 3.77(6H, s), 3.84(3H, s), 6.85(4H, d), 6.91(2H, d), 7.24(4H, d), 8.01(2H, d), 9.45–9.60(1H, br) |
| 52 | Me-C₆H₄- | Me-C₆H₄- | CN | (CH₂)₅ | COC₂H₅ | Syrup | 1.21(3H, t), 1.32–1.50(4H, m), 1.55–1.70(2H, m), 2.20(2H, t), 2.25–2.38(8H, m), 2.50(2H, q), 7.13(4H, d), 7.24(4H, d), 8.80–9.09(1H, br) |
| 53 | Me-C₆H₄- | Me-C₆H₄- | CN | (CH₂)₅ | COPh | Syrup | 1.39–1.50(4H, m), 1.60–1.80(2H, m), 2.25–2.39(10H, m), 7.14(4H, d), 7.25(4H, d), 7.47(2H, t), 7.59–7.68(1H, m), 8.09(2H, d), 9.10–9.25(1H, br) |
| 54 | F-C₆H₄- | F-C₆H₄- | CN | (CH₂)₅ | COC₂H₅ | Syrup | 1.23(3H, t), 1.31–1.50(4H, m), 1.55–1.76(2H, m), 2.15–2.38(4H, m), 2.52(2H, q), 7.06(4H, t), 7.25–7.37(4H, m), 8.70–8.95(1H, br) |

TABLE 20

$$Ar^1\text{-}C(Ar^2)(X)\text{-}Q\text{-}CONH\text{-}OR^1$$

| Cpd. No. | Ar¹ | Ar² | X | Q | R¹ | m.p. (°C.) | NMR (δ; CDCl₃) |
|---|---|---|---|---|---|---|---|
| 55 | F-C₆H₄- | F-C₆H₄- | CN | (CH₂)₅ | COPh | Syrup | 1.25–1.58(4H, m), 1.60–1.82(2H, m), 2.20–2.41(4H, m), 7.05(4H, t), 7.24–7.39(4H, m), 7.48(2H, t), 7.64(1H, t), 8.09(2H, d), 9.17(1H, br s) |
| 56 | MeO-C₆H₄- | MeO-C₆H₄- | CN | (CH₂)₅ | CONH₂ | Syrup | 1.30–1.48(4H, m), 1.50–1.69(2H, m), 2.10–2.33(4H, m), 3.77(6H, s), 5.55–5.90(2H, br), 6.85(4H, d), 7.24(1H, d), 8.70–9.80(1H, br) |

Formulation Example

| | |
|---|---|
| (1) Compound 32 | 50 mg |
| (2) Lactose | 34 mg |
| (3) Corn starch | 10.6 mg |
| (4) Corn starch (paste) | 5 mg |
| (5) Magnesium stearate | 0.4 mg |
| (6) Carboxymethylcellulose Ca | 20 mg |
| Total | 120 mg |

The above components were mixed and compressed using a tablet machine in the conventional manner.

Formulation Example 2

| | |
|---|---|
| (1) Compound 5 | 10.0 g |
| (2) Lactose | 60.0 g |
| (3) Corn starch | 35.0 g |
| (4) Gelatin | 3.0 g |
| (5) Magnesium stearate | 2.0 g |

Using a 10 weight % aqueous solution of gelatin (3.0 g), a mixture of the compound 5 (10.0 g), lactose (60.0 g) and corn starch (35.0 g) was granulated through a 1 mm-mesh sieve, dried at 40° C., and received. This granulation was mixed with 2.0 g of magnesium stearate and the mixture was compressed. The core tablets thus obtained were coated with a sugar-coating composition comprising an aqueous suspension of sucrose, titanium dioxide, talc, and gum arabic. The coated tablets were glazed with beeswax to provide 1000 finished tablets.

Experimental Example 1

Neutralizing effect on lipopolysaccharide (LPS)—induced cytotoxicity in a rat mixed cerebral cell culture system (LIC assay)

LPS, a substance known to activate glial cells (astrocytes, microglia), was added to a rat mixed cerebral cell culture system and the compounds which would neutralize the cytotoxicity induced by LPS were screened by the following method.

[Method]

(1) Neonatal rat mixed cerebral cell culture

From neonatal Crj:CD (SD) rats (1–3 day old, Charles-River Japan, Ltd), the brains were isolated and placed in ice-cooled D-MEM/10% FCS (Dulbecco's cell culture minimal essential medium supplemented with 10% of fetal calf serum, 100 units/ml of penicillin and 100 gg/ml of streptomycin). Then, mixed cerebral cell culture were treated in the following steps. Incidentally stating, ice-cooled D-MEM/10%FCS was used as the medium.

1. The cerebrum was separated from the enucleated brain and the meninges was removed under a stereoscopic microscope.

2. The cerebrums were placed in a nylon-mesh (100–200 μm) bag for filtration with the aid of a rubber policeman.

3. Using ice-cooled D-MEM/10% FCS, the cells were washed three times (1,000 rpm, 8 min.). Then, this cell suspension was subjected to filtration through a cell strainer (40 μm mesh, Falcon 2340) and the number of viable cells was counted by the trypan blue method.

4. The cells were seeded in a tissue-culture flask (96-well microtiter plate, Nunc) at a cell density of $1 \times 10_5$ cells/100 μl/well).

5. One week later, 100 μl/well of D-MEM/10% FCS was added.

6. The plate was further incubated for about 1 to 2 weeks and the neutralizing activity of the test compounds was evaluated by the following method.

(2) Evaluation of neutralizing activity

1. Following the rat mixed cerebral cell culture in (1) above (after 2–3 weeks of incubation), the medium was discarded from the respective wells of the 96-well microtiter plate, and 50 μl/well of fresh D-MEM/2% FCS was added.

2. A test sample and LPS (manufactured by Difco Inc., *E. coli* 011: B4, Bact) of an adequate concentration, 25 μl per well, were respectively added. D-MEM/2% FCS was employed as the medium.

As the test sample, each of the compounds shown in Table 21 was dissolved in DMSO at a concentration of $10^{-2}$M and the solution was diluted with D-MEM/2% FCS, which was used for assay.

3. After a suitable period (usually 4 to 5 days) of incubation, the degree of cytotoxic effect was assessed by the microscopic observation, and MTT method.

(3) MTT [3-(4,5-dimethylthiazol-2-yl)-2,5-diphenyltetrazolium bromide] method

MTT dissolved in a phosphate-buffered physiological saline solution (5 mg/ml, manufactured by Sigma Chemical Co.,) was added, 10 μl per well. After 4 to 6 hours of incubation (37° C., under 10% carbon dioxide gas phase), 100 μl/well of 0.01N HCl containing 10% SDS was added to thereby dissolve the formed formazan. After complete dissolution, the absorbance (wave-length 540–590 nm) was measure for each well.

The $ED_{50}$ values were determined by calculating the recovery rates by means of the following equation and plotting the concentrations of compounds giving a recovery rate of 50% on graph paper.

Recovery rate (%)=(C−B)×100/(A−B)

[A: the absorbance at 550 nm of the control well to which only the medium had been was added B: the absorbance at 550 nm of the well to which LPS had been added C: the absorbance at 550 nm of the well to which both LPS and the test compound had been added]

[Results]

The results are shown in Table 21.

TABLE 21

| Compound No. | $ED_{50}$ value ($\mu$M) |
| --- | --- |
| Compound 1 | 0.01 |
| Compound 3 | 0.01 |
| Compound 4 | 0.01 |
| Compound 11 | 0.01 |
| Compound 12 | 0.01 |
| Compound 13 | 0.01 |
| Compound 20 | 0.01 |
| Compound 21 | 0.01 |

It is apparent from the above date that the compounds of this invention neutralized the LPS-induced cytotoxicity and death of nerve cells at low concentrations, attesting to their remarkably high anti-neurodegenerative activity.

Experimental Example 2

Inhibitory effect on the apomorphine -induced circling behavior in rats pretreated with LPS infused into the unilateral striatum

[Method]

Male Wistar rats (8–9 week old) weighing 250–280 g at the operation for LPS infusion were submitted to this experiment.. Throughout the experimental period, the animals were group-fed in a vivarium controlled at 24±1° C. and 55±1% R.H., with a light-dark cycle of 12 hr (7:00–19:00 ON) and free access to food (Clea Japan, Inc., CE-2 solid pellets) and water (tap water).

Under pentobarbital (50 mg/kg, i.p.) anesthesia, the rat's head was immobilized in David Kopf's brain stereotaxic apparatus for small animal use and with reference to Pellegrino & Cushman's brain atlas, a 30 Gauge stainless steel needle was indwelled in the unilateral striatum (A8.2, L2.8, H4.3). The infusion volume of LPS was set at 5 μg. LPS was dissolved in 1 μl of a phosphate-buffered physiological saline solution (PBS, pH 7.2) and the solution was infused gradually at a speed of 0.2 μl/min. The infusion needle was kept in position till 3 minutes following infusion and withdrawn only after sufficient diffusion of the drug solution had taken place.

After 7–8 days postoperatively, 1 mg/kg of apomorphine was administered subcutaneously and the number of induced circling behavior during a 30-minute period immediately following administration were determined with an automatic counter.

The Compound 1 produced in Working Example 1 was suspended in 5% aqueous gum arabic solution, and the suspension was administered intraperitoneally at a dose of 0.2 ml per 100 g rat body weight. This administration was carried out three times, namely 30 minutes before infusion of 5 Rg LPS and 3 and 24 hours after the infusion. The control group was administered intraperitoneally with a physiological saline solution alone.

[Results]

The number of induced circling behavior in the test group administered with the Compound 1 was 41% relative to those in the control group.

It is apparent from this data that the compound of this invention significantly neutralized the LPS-induced cerebral tissue derangements, attesting to its remarkably high anti-neurodegenerative activity.

As a result of the foregoing, the inventors have determined that the compound (I) of this invention has excellent anti-neurodegenerative activity with a low toxicity and, therefore, is useful for the prophylaxis, therapy or improved prognosis of neurodegenerative diseases (e.g. Alzheimer's disease, Parkinson's disease, Down's syndrome, Pick's disease, Creutzfeldt-Jakob diseases, multiple sclerosis, bacterial or viral meningitis such as Borna disease, postvaccination encephalitis and AIDS-associated encephalopathy) and brain dysfunctions (e.g. cerebral infarction, cerebral hemorrhage, subarachinoid hemorrhage and trauma). These compound are also effective in cytokineassociated symptoms such as general malaise, fever, sleep, headache, arthralgia, anorexia and depression.

We claim:

1. A compound of the formula:

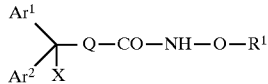

wherein

Ar$^1$ and Ar$^2$ independently represent phenyl;

Q represents a straight C$_{4-6}$ alkylene optionally having one sulfur atom;

R$^1$ is i) hydrogen, ii) an acyl group represented by the formula: —CO—R$^4$, —CONH—R$^4$, —CO—O—R$^4$, —CS—NH—R$^4$ or —CS—O—R$^4$ wherein R$^4$ is a) hydrogen or b) a C$_{1-6}$ alkyl, C$_{2-6}$ alkenyl, C$_{2-6}$ alkynyl, C$_{3-6}$ cycloalkyl, C$_{6-14}$ aryl or C$_{7-16}$ aralkyl group, each of which may be substituted by 1 to 5 substituents selected from the group consisting of halogen, C$_{1-3}$ alkylenedioxy, nitro, cyano, optionally halogenated C$_{1-6}$ alkyl, optionally halogenated C$_{3-6}$ cycloalkyl, optionally halogenated C$_{1-6}$ alkoxy, optionally halogenated C$_{1-6}$ alkylthio, hydroxyl, amino, mono-C$_{1-6}$ alkylamino, di-C$_{1-6}$ alkylamino, C$_{1-6}$ alkylcarbonyl, carboxyl, C$_{1-6}$ alkoxycarbonyl, carbamoyl, mono-C$_{1-6}$ alkylcarbamoyl, di-C$_{1-6}$ alkylcarbamoyl, sulfo, C$_{1-6}$ alkylsulfonyl, C$_{6-10}$ aryl, C$_{6-10}$ aryloxy iii) an acyl group represented by the formula: —SO$_2$—R$^{4a}$ or —SO—R$^{4a}$ wherein R$^{4a}$ is a C$_{1-6}$ alkyl, C$_{2-6}$ alkenyl, C$_{2-6}$ alkynyl, C36 cycloalkyl, C$_{6-14}$ aryl or C$_{7-16}$ aralkyl group, each of which may be substituted by 1 to 5 substituents selected from the group consisting of halogen, C$^{1-3}$ alkylenedioxy, nitro, cyano, optionally halogenated C$_{1-6}$ alkyl, optionally halogenated C$_{3-6}$ cycloalkyl, optionally halogenated C$_{1-6}$ alkoxy, optionally halogenated C$_{1-6}$ alkylthio, hydroxyl, amino, mono-C$_{1-6}$ alkylamino, di-C$_{1-6}$ alkylamino, C$_{1-6}$ alkylcarbonyl, carboxyl, C$_{1-6}$ alkoxycarbonyl, carbamoyl, mono-C$_{1-6}$ alkylcarbamoyl, di-C$_{1-6}$ alkylcarbamoyl, sulfo, C$_{1-6}$ alkylsulfonyl, C$_{6-10}$ aryl, C$_{6-10}$ aryloxy, iv) a C$_{1-6}$ alkyl, C$_{2-6}$ alkenyl, C$_{2-6}$ alkynyl, C$_{3-6}$ cycloalkyl, C$_{6-14}$ aryl or C$_{7-16}$ aralkyl group, each of which may be substituted by 1 to 5 substituents selected from the group consisting of halogen, C$_{1-3}$ alkylenedioxy, nitro, cyano, optionally halogenated C$_{1-6}$ alkyl, optionally halogenated C$_{3-6}$ cycloalkyl, optionally halogenated C$_{1-6}$ alkoxy, optionally halogenated C$_{1-6}$ alkylthio, hydroxyl, amino, mono-C$_{1-6}$ alkylamino, C$_{1-6}$ alkylcarbonyl, carboxyl, C$_{1-6}$ alkoxycarbonyl, carbamoyl, mono-C$_{1-6}$ alkylcarbamoyl, di-C$_{1-6}$ alkylcarbamoyl, sulfo, C$_{1-6}$ alkylsulfonyl, C$_{6-10}$ aryl, C$_{6-10}$ aryloxy, X is i) an electron-withdrawing group or ii) a C$_{6-14}$ aryl which may be substituted by 1 to 5 substituents selected from the group consisting of halogen, C$_{1-3}$ alkylenedioxy, nitro, cyano, optionally halogenated C$_{1-6}$ alkyl, optionally halogenated C$_{3-6}$ cycloalkyl, optionally halogenated C$_{1-6}$ alkoxy, optionally halogenated C$_{1-6}$ alkylthio, hydroxyl, amino, mon-C$_{1-6}$ alkylamino, d$_1$-C$_{1-6}$ alkylamino, C$_{1-6}$ alkylcarbonyl, carboxyl, C$_{1-6}$ alkoxycarbonyl, carbamoyl, mono-C$_{1-6}$ alkylcarbamoyl, d$_1$-C$_{1-6}$ alkylcarbamoyl, C$_{6-10}$ arylcarbamoyl, sulfo C$_{1-6}$ alkylsulfonyl, C$_{6-10}$ aryl, C$_{6-10}$ aryloxy, nono-C$_{1-6}$ alkylcarbamoyloxy and C$_{1-6}$ alkylcarboxamido, or a salt thereof.

2. A compound of claim 1 wherein X is a cyano group.

3. A compound of claim 1 wherein X is an acyl group represented by the formula: —CO—R$^4$, —CONH—R$^4$, —CO—O—R$^4$, —CS—NH—R$^4$, —CS—O—R$^4$, —SO$_2$R$^{4a}$ or —SO—R$^{4a}$.

4. A compound of claim 1, wherein X is an electron-withdrawing group.

5. A compound of claim 1, wherein R$^1$ is i) hydrogen, ii) an acyl group represented by the formula: —CO—R$^4$, —CONH—R$^4$, —CO—O—R$^4$, —CS—NH—R$^4$ or —CS—Q—R$^4$ wherein R4 is a) hydrogen or b) a C$_{1-6}$ alkyl, C$_{2-6}$ alkenyl, C$_{2-6}$ alkynyl, C$_{3-6}$ cycloalkyl, C$_{6-14}$ aryl or C$_{7-16}$ aralkyl group, each of which may be substituted by 1 to 5 substituents selected from the group consisting of halogen, C$_{1-3}$ alkylenedioxy, nitro, cyano, optionally halogenated C$_{1-6}$ alkyl, optionally halogenated C$_{3-6}$ cycloalkyl, optionally halogenated C$_{1-6}$ alkoxy, optionally halogenated C$_{1-6}$ alkylthio, hydroxyl, amino, mono-C$_{1-6}$ alkylamino, di-C$_{1-6}$ alkylamino, C$_{1-6}$ alkylcarbonyl, carboxyl, C$_{1-6}$ alkoxycarbonyl, carbamoyl, mono-C$_{1-6}$ alkylcarbamoyl, di-C$_{1-6}$ alkylcarbamoyl, sulfo, C$_{1-6}$ alkylsulfonyl, C$_{6-10}$ aryl, C$_{6-10}$ aryloxy, iii) an acyl group represented by the formula: —So$_2$—R$^{4a}$ or —SO—R$^{4a}$ wherein R$^{4a}$ is a C$_{1-6}$ alkyl, C$_{2-6}$ alkenyl, C$_{2-6}$ alkynyl, C$_{3-6}$ cycloalkyl, C$_{6-14}$ aryl or C$_{7-16}$ aralkyl group, each of which may be substituted by 1 to 5 substituents selected from the group consisting of halogen, C$_{1-3}$ alkylenedioxy, nitro, cyano, optionally halogenated C$_{1-6}$ alkyl, optionally halogenated C$_{3-6}$ cycloalkyl, optionally halogenated C$_{1-6}$ alkoxy, optionally halogenated C$_{1-6}$ alkylthio, hydroxyl, amino, mono-C$_{1-6}$ alkylamino, di-C$_{1-6}$ alkylamino, C$_{1-6}$ alkylcarbonyl, carboxyl, C$_{1-6}$ alkoxycarbonyl, carbamoyl, mono-C$_{1-6}$ alkylcarbamoyl, di-C$_{1-6}$ alkylcarbamoyl, sulfo, C$_{1-6}$ alkylsulfonyl, C$_{6-10}$ aryl, C$_{6-10}$ aryloxy, or iv) a C$_{1-6}$ alkyl which may be substituted by 1 to 5 substituents selected from the group consisting of halogen, C$_{1-3}$ alkylenedioxy, nitro, cyano, optionally halogenated C$_{1-6}$ alkyl, optionally halogenated C$_{3-6}$ cycloalkyl, optionally halogenated C$_{1-6}$ alkoxy, optionally halogenated $C_{1-6}$ alkylthio, hydroxyl, amino, mono-$C_{1-6}$ alkylamino, $C_{1-6}$ alkylcarbonyl, carboxyl, $C_{1-6}$ alkoxycarbonyl, carbamoyl, mono-$C_{1-6}$ alkylcarbamoyl, di-$C_{1-6}$ alkylcarbamoyl, sulfo, $C_{1-6}$ alkylsulfonyl, $C_{6-10}$ aryl, $C_{6-10}$ aryloxy.

6. A compound of claim 1, wherein $R^1$ is i) hydrogen, ii) an acyl group represented by the formula: —Co—$R^4$, —CONH—$R^4$, —CO—$R^4$, —CS—NH—$R^4$ or —CS—O—$R^4$ wherein $R^4$ is a) hydrogen or b) a $C_{1-6}$ alkyl, $C_{2-6}$ alkenyl, $C_{2-6}$ alkynyl, $C_{3-6}$ cycloalkyl, $C_{6-14}$ aryl or $C_{7-16}$ aralkyl group, each of which may be substituted by 1 to 5 substituents selected from the group consisting of halogen, $C_{1-3}$ alkylenedioxy, nitro, cyano, optionally halogenated $C_{1-6}$ alkyl, optionally halogenated C3-6 cycloalkyl, optionally halogenated $C_{1-6}$ alkoxy, optionally halogenated $C_{1-6}$ alkylthio, hydroxyl, amino, mono-$C_{1-6}$ alkylamino, di-$C_{1-6}$ alkylamino, $C_{1-6}$ alkylcarbonyl, carboxyl, $C_{1-6}$ alkoxycarbonyl, carbamoyl, mono-$C_{1-66}$ alkylcarbamoyl, di-$C_{1-6}$ alkylcarbamoyl, sulfo, $C_{1-6}$ alkylsulfonyl, $C_{6-10}$ aryl, $C_{6-10}$ aryloxy, iii) an acyl group represented by the formula: —$SO_2$-$R^{4a}$ or —SO—$R^{4a}$ wherein $R^{4a}$ is a $C_{1-6}$ alkyl, $C_{2-6}$ alkenyl, $C_{2-6}$ alkynyl, $C_{3-6}$ cycloalkyl, $C_{6-14}$ aryl or C0-,6 aralkyl group, each of which may be substituted by 1 to 5 substituents selected from the group consisting of halogen, $C_{1-3}$ alkylenedioxy, nitro, cyano, optionally halogenated $C_{1-6}$ alkyl, optionally halogenated $C_{3-6}$ cycloalkyl, optionally halogenated $C_{1-6}$ alkoxy, optionally halogenated $C_{1-6}$ alkylthio, hydroxyl, amino, mono-$C_{1-6}$ alkylamino, di-$C_{1-6}$ alkylamino, $C_{1-6}$ alkylcarbonyl, carboxyl, $C_{1-6}$ alkoxycarbonyl, carbamoyl, mono-$C_{1-6}$ alkylcarbamoyl, di-$C_{1-6}$ alkylcarbamoyl, sulfo, $C_{1-6}$ alkylsulfonyl, $C_{6-10}$ aryl, $C_{6-10}$ aryloxy, or iv) a $C_{1-6}$ alkyl group.

7. A compound selected from the group consisting of 7-cyano-7,7-diphenylheptanohydroxamic acid, 7,7-bis(4-methoxyphenyl)-7-cyanoheptanohydroxamic acid, 7,7-bis(4-fluorophenyl)-7-cyanoheptanohydroxamic acid, O-propionyl-7-cyano-7,7-diphenylheptanohydroxamic acid, O-propionyl-7,7-bis(4-methoxyphenyl)-7-cyanoheptanohydroxamic acid, O-propionyl-7,7-bis(4-fluorophenyl)-7-cyanoheptanohydroxamic acid, O-benzoyl-7-cyano-7,7-diphenylheptanohydroxamic acid, O-benzoyl-7,7-bis(4-methoxyphenyl)-7-cyanoheptanohydroxamic acid, O-benzoyl-7,7-bis(4-fluorophenyl)-7-cyanoheptanohydroxamic acid, 7-cyano-7,7-bis(4-ethoxyphenyl)heptanohydroxamic acid, and 7-cyano-7,7-bis[4-(2,2,2-trifluoroethoxyphenyl)]heptanohydroxamic acid, or a salt thereof.

8. A pharmaceutical composition which comprises a compound of claim 1 together with a pharmaceutically acceptable carrier.

9. A process for producing a compound of claim 1, which comprises reacting a compound of the formula:

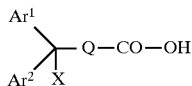

or a salt thereof or a reactive derivative thereof at the carboxyl group with hydroxylamine, and if necessary, allowing the resultant compound to react with a compound of the formula:

wherein

Y represents a leaving group and $R^{1a}$ a represents an acyl group or an optionally substituted hydrocarbon group or a salt thereof.

10. A composition of claim 8 which is useful for treating multiple sclerosis.

11. A composition of claim 8 which is useful for treating Alzheimer's disease.

12. A method of treating neurodegenerative diseases in mammals comprising administering to a subject in need of such treatment a therapeutically effective amount of a compound of claim 1.

* * * * *

UNITED STATES PATENT AND TRADEMARK OFFICE
CERTIFICATE OF CORRECTION

PATENT NO. : 5,891,916

DATED : April 6, 1999

INVENTOR(S) : KANEYOSHI KATO ET AL.

It is certified that error appears in the above-identified patent and that said Letters Patent is hereby corrected as shown below:

ON THE TITLE PAGE

[54] "HYDROXAMIX" should read --HYDROXAMIC--.

COLUMN 1

Line 1, "HYDROXAMIX" should read -- HYDROXAMIC--;
   Line 11, "Alzheimerrs" should read --Alzheimer's--;
   Line 26, "cytol,ines" should read --cytokines--; and
   Line 52, "state" should read --states--.

COLUMN 5

Line 22, "$C_{1-6}$ alkoxy," should read --$C_{1-6}$ alkoxy,--.

COLUMN 6

Line 27, "C3-6 cycloalkyl," should read --$C_{3-6}$ cycloalkyl,--; and
   Line 63, "C3-6" should read --$C_{3-6}$--.

COLUMN 7

Line 21, "—SO—R" should read ---SO—$R^{4a}$ --.

COLUMN 9

Line 10, "example" should read --examples--.

UNITED STATES PATENT AND TRADEMARK OFFICE
CERTIFICATE OF CORRECTION

PATENT NO. : 5,891,916

DATED : April 6, 1999

INVENTOR(S) : KANEYOSHI KATO ET AL.

It is certified that error appears in the above-identified patent and that said Letters Patent is hereby corrected as shown below:

COLUMN 11

Line 35, "compounds" should read --compound--; and
Line 38, "$C_{1-6}$" should read --$C_{1-16}$--.

COLUMN 12

Line 9, "di-$C_{16}$ alkylcarbamoyl" should read
--di-$C_{1-6}$ alkylcarbamoyl--; and
Line 34, "may the" should read -- may be the--.

COLUMN 13

Line 5, "group" should read --groups--;
Line 28, "group" should read --groups--;
Line 29, "group" should read --groups--;
Line 35, "ones" should read --one--;
Line 47, "$C_{13}$ alkylenedioxy" should read
--$C_{1-3}$ alkylenedioxy--; and
Line 62, "—CO—O—$R_4$," should read ---CO-O-$R^4$,--.

COLUMN 14

Line 23, "di-$C_{1-6}$ alkylcar-" should read
--di-$C_{1-6}$ alkylcar- --; and
Line 32, "4-quinoly," should read --4-quinolyl,--.

UNITED STATES PATENT AND TRADEMARK OFFICE
CERTIFICATE OF CORRECTION

PATENT NO. : 5,891,916

DATED : April 6, 1999

INVENTOR(S) : KANEYOSHI KATO ET AL.

It is certified that error appears in the above-identified patent and that said Letters Patent is hereby corrected as shown below:

COLUMN 15

Line 34, "salts" should read --salt--.

COLUMN 16

Line 2, "ones" should read --one--; and
  Line 33, "is" should read --there are--.

COLUMN 17

Line 27, "($I^a$). The" should read --($I^a$). ¶ The--; and
  Line 63, "nitrites" should read --nitriles--.

COLUMN 19

Line 4, "nitrites" should read --nitriles--;
  Line 9, "nitrites" should read --nitriles--;
  Line 40, "form" should read --from--; and
  Line 64, "nitrites," should read --nitriles,--.

COLUMN 21

Line 3, "also" should read --are also--.

COLUMN 22

Line 11, "a" should be deleted.
  Line 62, "phiLic" should read --philic--.

UNITED STATES PATENT AND TRADEMARK OFFICE
CERTIFICATE OF CORRECTION

PATENT NO. : 5,891,916
DATED      : April 6, 1999
INVENTOR(S): KANEYOSHI KATO ET AL.

It is certified that error appears in the above-identified patent and that said Letters Patent is hereby corrected as shown below:

COLUMN 31

Line 59, "Ethyl B" should read --Ethyl 8--.

COLUMN 34

Line 30, "2,2 mmol.)" should read --2.2 mmol.)--.

COLUMN 35

Table 6, "$(CH_2)_5$" should read --$(CH_2)_6$--.

COLUMN 37

Line 50, "Compound 7:  7,7" should read --Compound 7: 7,7--.

COLUMN 38

Line 51, "-7.,7-" should read -- -7,7- --.

COLUMN 39

Line 44, "Compound 37:  4-cyano-" should read --Compound 37: 4-cyano- --.

UNITED STATES PATENT AND TRADEMARK OFFICE
CERTIFICATE OF CORRECTION

PATENT NO. : 5,891,916

DATED : April 6, 1999

INVENTOR(S): KANEYOSHI KATO ET AL.

It is certified that error appears in the above-identified patent and that said Letters Patent is hereby corrected as shown below:

COLUMN 40

Line 3, "ethyl.acetate." should read --ethyl acetate.--;
Line 11, "added" should read --added to--; and
Line 15, "iN HCl" should read --1N HCl--.

COLUMN 41

Line 20, "2)3,3,3-Triphenylpropanal To" should read
--2)3,3,3-Triphenylpropanal ¶ To--.

COLUMN 42

Line 29, "2," should read --8,--.

COLUMN 46

Table 11, "7.30." should read --7.30--; and
Table 11, "brs)" should read --br s)--.

COLUMN 48

Table 12, "745" should read --7.45--.

COLUMN 56

Table 20, "7.24(1H,d)," should read --7.24(4H,d),--.

UNITED STATES PATENT AND TRADEMARK OFFICE
CERTIFICATE OF CORRECTION

PATENT NO. : 5,891,916

DATED : April 6, 1999

INVENTOR(S) : KANEYOSHI KATO ET AL.

It is certified that error appears in the above-identified patent and that said Letters Patent is hereby corrected as shown below:

COLUMN 57

Line 2, "received." should read --resieved.--;
Line 25, "gg/ml" should read --$\mu$g/ml--;
Line 26, "were" should read --was--; and
Line 40, "1x10$_5$" should read --1x10$^5$--.

COLUMN 58

Line 5, "measure" should read --measured--; and
Line 66, "were" should read --was--.

COLUMN 59

Line 6, "Rg" should read --$\mu$g--;
Line 28, "compound" should read --compounds--; and "cytokineassociated" should read --cytokine-associated--;
Line 60, "C36 cycloalkyl," should read --$C_{3-6}$ cycloalkyl,-- and
Line 63, "C$^{1-3}$ alkylenedioxy," should read --$C_{1-3}$ alkylenedioxy,--.

COLUMN 60

Line 22, "mon-$C_{1-6}$" should read --mono-$C_{1-6}$--;
Line 23, "d$_1$-$C_{1-6}$ alkylamino," should read --di-$C_{1-6}$ alkylamino,--

UNITED STATES PATENT AND TRADEMARK OFFICE
CERTIFICATE OF CORRECTION

PATENT NO. : 5,891,916

DATED : April 6, 1999

INVENTOR(S): KANEYOSHI KATO ET AL.

It is certified that error appears in the above-identified patent and that said Letters Patent is hereby corrected as shown below:

COLUMN 60 (Contd.)

Line 25, "d$_1$-C$_{1-6}$ alkylcarbamoyl," should read --di-C$_{1-6}$ alkylcarbamoyl,--;
Line 27, "nono-C$_{1-6}$ alkylcarbamoyloxy" should read --mono-C$_{1-6}$ alkylcarbamoyloxy--;
Line 40, "-CS-Q-R$^4$" should read -- -CS-O-R$^4$--; and "R4" should read --R$^4$--; and
Line 52, "-So$_2$-R$^{4a}$" should read --SO$_2$-R$^{4a}$--.

COLUMN 61

Line 7, "—Co—R$^4$," should read -- —CO-R$^4$,--;
Line 8, "—CO—R$^4$," should read -- —CO-O-R$^4$,--;
Line 14, "C3-6" should read --C$_{3-6}$--;

UNITED STATES PATENT AND TRADEMARK OFFICE
CERTIFICATE OF CORRECTION

PATENT NO. : 5,891,916

DATED : April 6, 1999

INVENTOR(S) : KANEYOSHI KATO ET AL.

It is certified that error appears in the above-identified patent and that said Letters Patent is hereby corrected as shown below:

<u>COLUMN 61 (Contd.)</u>

Line 18, "mono-$C_{1-66}$ alkylcarbamoyl," should read --mono-$C_{1-6}$ alkylcarbamoyl,--and
Line 22, "CO-,6" should read --$C_{7-16}$--.

Signed and Sealed this

Second Day of May, 2000

Attest:

Q. TODD DICKINSON

*Attesting Officer*   *Director of Patents and Trademarks*